(12) United States Patent
Furusho

(10) Patent No.: US 7,597,339 B2
(45) Date of Patent: Oct. 6, 2009

(54) WHEELCHAIR

(76) Inventor: Eiko Furusho, 76-23, Hanazono 7-chome, Kumamoto-shi (JP) 8600072

( * ) Notice: Subject to any disclaimer, the term of this patent is extended or adjusted under 35 U.S.C. 154(b) by 0 days.

(21) Appl. No.: 11/883,680

(22) PCT Filed: Feb. 8, 2006

(86) PCT No.: PCT/JP2006/302124
§ 371 (c)(1),
(2), (4) Date: Sep. 26, 2007

(87) PCT Pub. No.: WO2006/087947
PCT Pub. Date: Aug. 24, 2006

(65) Prior Publication Data
US 2008/0111340 A1  May 15, 2008

(30) Foreign Application Priority Data
Feb. 15, 2005  (JP)  ............................ 2005-038126
Apr. 5, 2005  (JP)  ............................ 2005-108875
Oct. 13, 2005  (JP)  ............................ 2005-299364

(51) Int. Cl.
*A61G 5/10* (2006.01)
(52) U.S. Cl. ............................... 280/304.1; 280/288.4
(58) Field of Classification Search ............... 280/304.1, 280/288.4
See application file for complete search history.

(56) References Cited

U.S. PATENT DOCUMENTS

| 4,831,644 | A | * | 5/1989 | Lopez | ......................... 378/178 |
| 5,244,222 | A | * | 9/1993 | Benoit | ..................... 280/250.1 |
| 5,690,387 | A | * | 11/1997 | Sarti | .......................... 297/397 |
| 6,322,250 | B1 | * | 11/2001 | Pratt | .......................... 378/208 |
| 2005/0077760 | A1 | * | 4/2005 | Smith | ........................... 297/42 |
| 2005/0121961 | A1 | * | 6/2005 | Beauchesne et al. | ........ 297/353 |

FOREIGN PATENT DOCUMENTS

| JP | 5-11923 | 2/1993 |
| JP | 10-85262 | 4/1998 |
| JP | 2003-235907 | 8/2003 |
| JP | 2004-329467 | 11/2004 |

* cited by examiner

*Primary Examiner*—Paul N Dickson
*Assistant Examiner*—Tashiana Adams
(74) *Attorney, Agent, or Firm*—Jordan and Hamburg LLP

(57) ABSTRACT

A wheelchair is capable of radiographing with the wheelchair as is by using a general radiographic device, without a need to switch to a different chair. The wheelchair includes a seat portion, a backrest portion provided with upper frame bodies mounted approximately perpendicular to the seat portion and a main body detachably mounted to the upper frame bodies transversely of the upper frame bodies, holding portions installed consecutively to the upper frame bodies, and wheels. The upper frame bodies are approximately perpendicular to the ground plane of the wheels, the main body is configured of an X-ray transmissive material, and the holding portions are installed consecutively to the upper frame bodies detachably and turnably.

16 Claims, 17 Drawing Sheets

(a)

(b)

(a)

(b)

(a)

(b)

(a)

(b)

WHEELCHAIR

TECHNICAL FIELD

The present invention relates to a wheelchair. More specifically, the present invention relates to a wheelchair capable of being used, normally, for moving and so on similar to a general wheelchair, and at the time of radiographing, radiographing with the wheelchair as is by using a general radiographic device, such as Lieder's radiographic stand, Bucky's radiographic table, or the like, in seated, semi-seated, and recumbent positions in the anteroposterior (front) direction, the lateral direction, and the oblique direction, without a need to switch to a different chair. The present invention relates also to a wheelchair appropriate for radiographing a lower limb by using the wheelchair as a radiographic unit, in particular, radiographing in the anteroposterior direction of a flexed knee that cannot be straightened.

BACKGROUND OF THE INVENTION

Diagnosis or medical treatment by radiography is performed for persons who indispensably use wheelchairs due to age or persons who use wheelchairs due to physical disabilities.

In this case, the person who uses the wheelchair once gets off from the wheelchair and sits again in a chair situated in front of Lieder's radiographic stand for radiographing a person in a standing position, or that person is moved to Bucky's radiographic table or the like for radiographing.

However, it is difficult to move persons whose activities are limited, such as a person with a broken bone, and seat them in a different chair or allow the person to move to a different radiographic table or stand. Further, time for getting a radiographed person out of the wheelchair is needed, and a care provider who assists the radiographed person must be arranged. Thus, it requires a great amount of labor.

Therefore, various technologies capable of radiographing the radiographed person who uses a wheelchair without a need for getting the person out of the wheelchair have been proposed (see Patent Document 1, for example). FIG. 17 shows an entire schematic lateral view of a conventional radiography-use wheelchair. In FIG. 17, in the conventional radiography-use wheelchair, a holder 103 of a cassette 102 containing a radiographic film is inserted into lifting-adaptable rails equipped behind a hand-gilding handgrip frame 101, and as a result of an operation of a remote control lever 104, an upright-to-lying conversion can be performed, in which the hand-gilding handgrip frame 101 in an upright state is turned about a fulcrum pin 105 relative to a wheelchair frame 106, resulting in a lying state, which leads to the formation of an overall bed, together with the wheelchair frame 106 and a footrest 107.

Patent Document 1: Japanese Published Unexamined Patent Application No. 2004-329467

DISCLOSURE OF THE INVENTION

Problem to be Solved by the Invention

However, in the conventional radiography-use wheelchair, the cassette containing the radiographic film is mounted to a backrest portion of the wheelchair, and thus, it is possible to radiograph a chest portion. When a radiographic position of the radiographed person is adjusted to appropriately radiograph the person, the radiographed person needs to be moved within the wheelchair. Thus, it is difficult to exactly position for radiography. In particular, it is difficult to radiograph in the oblique direction and the lateral direction.

Alternatively, when a lower limb is radiographed, in particular, when a flexed knee that cannot be straightened is radiographed from the anteroposterior (front) direction, it is difficult to radiograph by bringing the cassette close to the knee.

In the conventional radiography-use wheelchair, a radiography-use cassette holder and the like are mounted to the wheelchair, and in addition, one portion of the backrest portion cannot be accommodated. Thus, the wheelchair is heavy and large, and therefore, it is difficult to place the wheelchair in a hospital or a hospital room or other places, or use for ordinary movement like an ordinary wheelchair. Further, when a person who uses the wheelchair is radiographed, the person purposely needs to be moved to sit in a conventional radiography-use wheelchair or moved to a different radiographic table or stand. Thus, it is, in particular, difficult to radiograph a person whose activities are limited, such as a person with a broken bone or other persons.

In view of the foregoing problems, the present invention has been achieved as an easy-to-use comfortable wheelchair that is lightweight and small in size, and an object thereof is to provide a wheelchair capable of being used, normally, for moving and so on, similar to a general wheelchair, and at the time of radiographing, radiographing with the wheelchair as is by using a general radiographic device, such as Lieder's radiographic stand, Bucky's radiographic table, or the like, without a need to switch to a different chair.

Means of Solving the Problems

To achieve the foregoing object, a wheelchair of the present invention includes: a seat portion; a backrest portion provided with backrest columns mounted approximately perpendicular to the seat portion and a main body detachably mounted to the backrest columns transversely of the backrest columns; holding portions installed consecutively to the backrest columns; wheels; front lower columns connected to the wheels, approximately perpendicular to a ground plane of the wheels; and rear lower columns connected to the wheels, approximately perpendicular to the ground plane of the wheels. The backrest columns are approximately perpendicular to a ground plane of the wheels, the main body is configured of an X-ray transmissive material, the backrest columns are installed consecutively and linearly to the rear lower columns, and the holding portions are installed consecutively to the backrest columns detachably and turnably.

Herein, the backrest columns of the backrest portion are approximately perpendicular to the ground plane of the wheels, the backrest columns are installed consecutively and linearly to the rear lower columns, and the holding portions are installed consecutively to the backrest columns detachably and turnably. Thus, Lieder's radiographic stand and a body of a radiographed person can be brought approximately parallel and adhere to each other, for example. As a result, a sharp radiogram can be obtained. Further, the main body of the backrest portion is detachably mounted to the backrest columns and is configured of the X-ray transmissive material. Thus, an X-ray can be easily transmitted to the radiographic unit, and as a result, a sharp radiogram can be obtained.

The sear portion may be approximately parallel to the ground plane of the wheels.

The wheelchair of the present invention includes right and left armrests including armrest columns mounted approximately perpendicular to the seat portion, wherein the backrest columns are installed approximately perpendicular to the ground plane of the wheels and consecutively to the rear lower columns detachably, the armrest columns are installed approximately perpendicular to the ground plane of the wheels and consecutively to the front lower columns detachably, and the wheels are mounted on extended lines of the front lower columns and the rear lower columns, thus, Lieder's radiographic stand and a body of the radiographed person, in particular, the lateral side thereof, can be brought approximately parallel and adhere to each other, for example. As a result, a sharp radiogram can be obtained. Further, the main body of the backrest portion is detachably mounted to the backrest columns and is configured of an X-ray transmissive material. Thus, an X-ray can be easily transmitted to the radiographic unit, and as a result, a sharp radiogram can be obtained.

The backrest branched columns may be mounted to the backrest columns, and the space may be formed between the backrest columns and the backrest branched columns.

The holding portions may be curved, and holding-portion adjustment knobs capable of turning the holding portions and removing the holding portions may be mounted to the holding portions in a direction approximately the same as a direction into which the holding portions are curved.

The main body may be detachably covered with a cover, and the main body and the cover have flexibility.

The wheelchair of the present invention includes right and left armrests including armrest columns mounted approximately perpendicular to the seat portion, leg members extended forward from the front lower columns; and footrests mounted to the leg members. When the wheelchair includes first support members each arranged below the seat portion so as to face each other and having a first lateral member arranged in an opposed spatial area being detachably mounted, and second support members each arranged forward of the front lower columns so as to face each other and having a second lateral member arranged in an opposed spatial area being detachably mounted, it becomes possible, by using the first support members and the second support members, to support the cassette (image receiving portion) used for radiography near the back of a knee of the radiographed person who sits in the wheelchair.

When the wheelchair of the present invention is configured such that each of the front lower columns and the rear lower columns is expandable and contractable, even when a wheel of the wheelchair rides up over a structural object or the like so that the seat portion is tilted relative to the ground plane, in this case, the front lower columns or the rear lower columns to which the rode-up wheel is mounted are shortened or the front lower columns or the rear lower columns to which non-ridden-up wheels are mounted are expanded to thereby bring the seat portion approximately parallel to the ground plane.

Alternatively, when the wheelchair of the present invention is configured such that the right and left armrests and the backrest columns are kept apart and the backrest columns are, at its ends, arranged to be detachable and turnable relative to the seat portion, the backrest portion can be tilted backward, and thus, it is possible for a person who sits in the wheelchair to assume a relaxed posture while traveling. Further, it is possible to radiograph a person who finds difficulty in maintaining a sitting position while remaining seated in the wheelchair in a semi-sitting or a recumbent position at the time of not only traveling but also radiographing.

In the wheelchair of the present invention, when the footrests are turnably mounted to the leg members, and the footrests have surfaces on which feet are placed and surfaces opposed to the surfaces on which the feet are placed, the surfaces opposed to the surfaces on which the feet are placed are configured to have holding members for holding a cassette (image receiving portion) being detachably mounted thereon and the footrests are turned so as to be approximately perpendicular to the ground plane, the surfaces opposed to the surfaces on which the feet are placed are located on approximately the same plane as the second support members. In this case, the cassette (image receiving portion) can be arranged on the lateral side of the lower limb along the lateral surface of the wheelchair.

Alternatively, when the wheelchair of the present invention is configured such that the footrests are movably mounted to the leg members, even when a tall radiographed person sits, the footrests can be moved forward to place his or her feet on the footrests even if the legs are stretched. As a result, the knee position is lowered, which makes it easier to radiograph the lower limb.

In the wheelchair of the present invention, when the seat portion is configured of an X-ray transmissive material, it is possible to radiograph a thigh by arranging the cassette (image receiving portion) immediately below the seat portion.

When the wheelchair of the present invention is configured such that the first support members are formed with a plurality of holes, the holes next to one another differ in shape and the holes opposed to each other are the same in shape, it becomes possible to easily find the opposed hole on one side after a rod member or first lateral member is inserted into the hole on the other side, for example.

Effect of the Invention

A wheelchair according to the present invention is lightweight and small in size, easy to use, and comfortable. Normally, the wheelchair can be used for moving or other purposes as in the case of a general wheelchair. At the time of radiographing, it is possible to radiograph with the wheelchair as is by using general radiographic devices, such as Lieder's radiographic stand, Bucky's radiographic table, or the like, without a need to switch to a different chair.

DESCRIPTION OF REFERENCE NUMERALS

Figure 1:
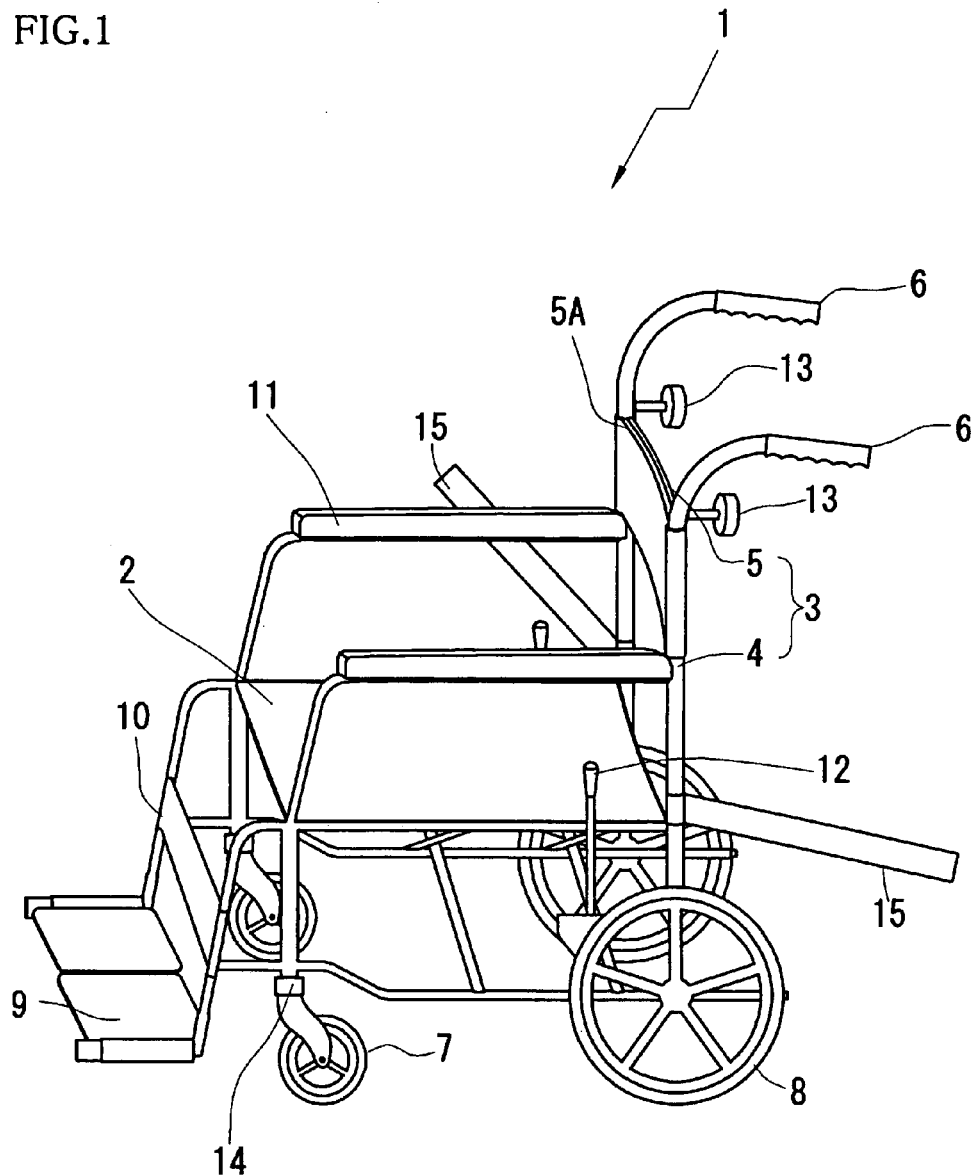
FIG. 1 is a schematic explanatory diagram showing a first example of a wheelchair to which the present invention is applied.

1 Wheelchair
2 Seat portion
3 Backrest portion
4 Upper frame body
4A Upper branched frame body
4B Upper frame body cover
5 Main body
5A Cover
6 Holding portion
7 Front wheel
8 Rear wheel
9 Footrest
10 Leg-rest
11 Armrest
11A Frame member
12 Brake
13 Holding-portion adjustment knob
14 Lower-frame-body expansion and contraction fitting
15 Seatbelt
16 Reinforcement pipe
17 Fixing screw
18 Lower frame body
18A Lower branched frame body
18B Leg frame body
19 Accommodating pipe
20 Lieder's radiographic stand
21 Cassette (image receiving portion)
22 X-ray radiation direction
22A Radiographic unit support device
22B Radiographic unit
23 First support member
23A First hole
24 First rod member (first lateral member)
25 Second support member
25A Second hole
26 Second rod member (second lateral member)
27 Support plate
27A Hole
28 Footrest support rod
28A Height adjustment device
29 Cassette holder
30 Holding member
31 Below-knee region
32 Knee region
33 Pillow portion
34 Headrest
35 Pillow-portion frame body
36 Grip
37 Joint portion
38 Setscrew
39 Fixing screw
40 Thread
41 Locking screw Best Mode for Carrying out the Invention Hereinafter, embodiments of the present invention are described with reference to the drawings to facilitate understanding of the present invention. FIG. 1 is a schematic explanatory diagram showing a first example of a wheelchair to which the present invention is applied. A wheelchair 1 to which the present invention is applied is configured of a seat portion 2; a backrest portion 3 including upper frame bodies 4 mounted approximately perpendicular to the seat portion and a main body 5 mounted to the upper frame bodies transversely of the upper frame bodies; holding portions 6 installed consecutively to the upper frame bodies; front wheels 7; rear wheels 8 of 12 inches (30.5 cm) in diameter; footrests 9 for supporting feet; a leg-rest 10 for supporting lower limbs so that the lower limbs do not fall backward; armrests 11; brakes 12; holding-portion adjustment knobs 13 capable of turning the holding portions and removing the holding portions; lower-frame-body expansion and contraction fittings 14 capable of adjusting the seat portion such that the lower frame bodies located below the seat portion are expanded and contracted so that a predetermined angle is formed relative to a ground plane of the wheel; and seatbelts 15 configured of an X-ray transmissive material such as cotton, carbon, or the like. The frame bodies of the backrest portion are approximately perpendicular to the ground plane of the wheels. A fabric or the main body 5 of the backrest portion, which is detachably mounted to the upper frame bodies and configured of an X-ray transmissive material such as cotton, carbon, or the like, is further covered detachably with a cover 5A, such as a fabric made of a thick texture, excellent in durability. The main body 5 and the cover 5A both have flexibility. It is noted that the "predetermined angle" is an angle formed such that the seat portion is tilted in the back-and-forth and right-and-left directions.

Herein, as long as the upper frame bodies of the backrest portion are approximately perpendicular to the ground plane of the wheels, the main body of the backrest portion is detachably mounted and configured of the X-ray transmissive material, and the holding portions are installed consecutively to the upper frame bodies detachably and turnably, the fabric configured of the X-ray transmissive material may not necessarily be covered detachably with the fabric excellent in durability. Alternatively, the main body may not necessarily be a fabric and may not necessarily have the flexibility, either. The holding-portion adjustment knobs, the lower-frame-body expansion and contraction fittings, and the seatbelts may not necessarily be mounted to the wheelchair, and the diameter of the rear wheels may not necessarily be 30.5 cm. The brakes may be mounted to the front wheels.

Upon movement in the wheelchair, for the reason that it becomes possible to seat a person sitting in the wheelchair more stably, it is preferable that a seatbelt configured of a fabric made of a thick texture or the like be mounted to the wheelchair, in addition to the seatbelt configured of the X-ray transmissive material such as cotton, carbon, or the like.

Figure 2:
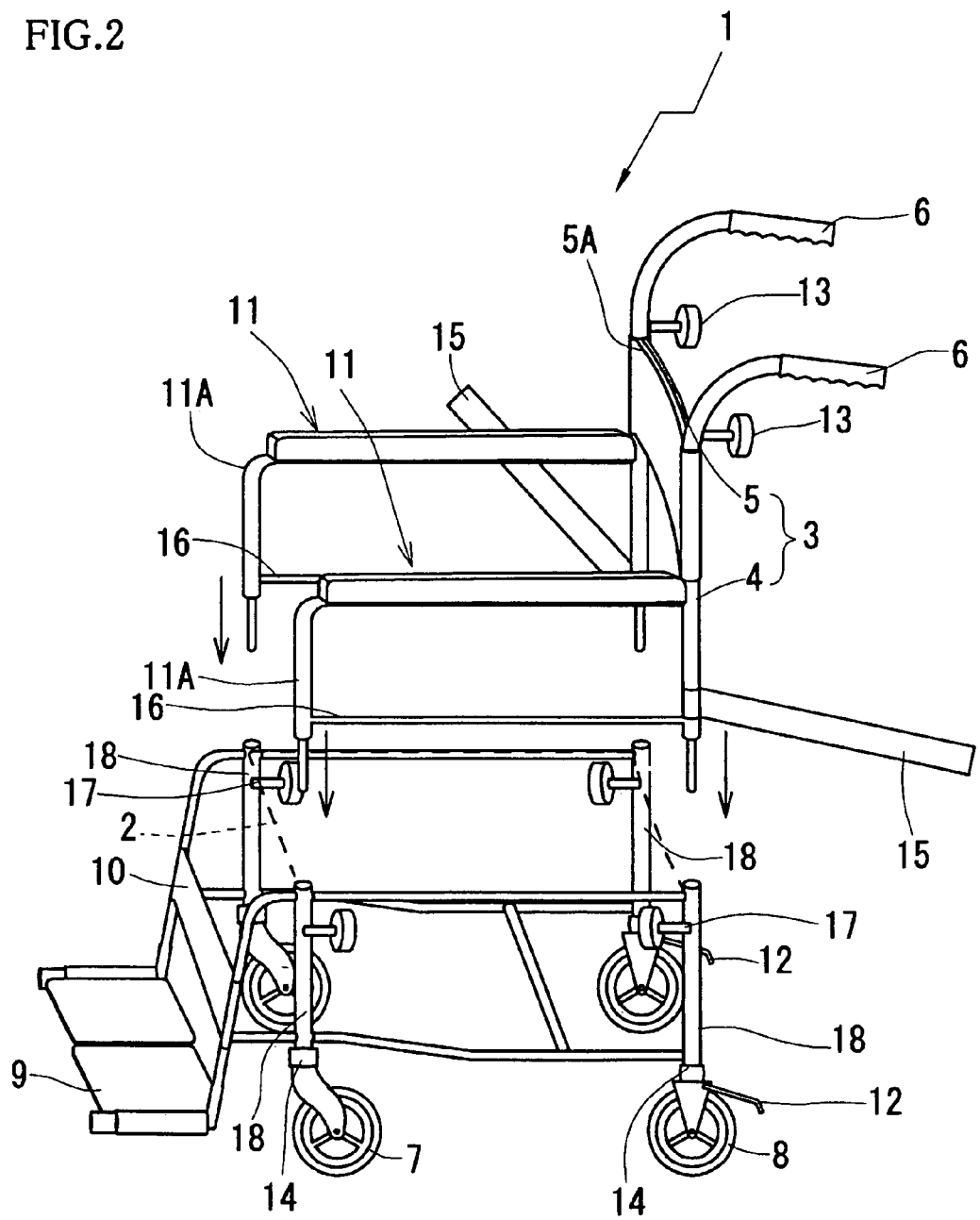
FIG. 2 is a schematic explanatory diagram showing a second example of a wheelchair to which the present invention is applied.

FIG. 2 is a schematic explanatory diagram showing a second example of a wheelchair to which the present invention is applied. The wheelchair 1 to which the present invention is applied is configured of: the seat portion 2; the backrest portion 3 including the upper frame bodies 4 mounted approximately perpendicular to the seat portion and the main body 5 mounted to the upper frame bodies transversely of the upper frame bodies; the holding portions 6 installed consecutively to the upper frame bodies; the armrests 11 including frame members 11A approximately parallel to the upper frame bodies; the front wheels 7; the rear wheels 8 in which the brakes 12 are mounted; lower frame bodies 18 approximately perpendicular to the ground plane of the wheels; the footrests 9 for supporting feet; the leg-rest 10 for supporting lower limbs so that the lower limbs do not fall backward; the holding-portion adjustment knobs 13 capable of turning the holding portions and removing the holding portions; the lower-frame-body expansion and contraction fittings 14 for expanding and contracting the lower frame bodies located below the seat portion; and the seatbelts 15 configured of an X-ray transmissive material such as cotton, carbon, or the like; and reinforcement pipes 16 for connecting the upper frame bodies 4 and the frame members 11A of the armrests 11.

The upper frame bodies of the backrest portion are approximately perpendicular to the ground plane of the wheels. A fabric or the main body 5 of the backrest portion, which is detachably mounted to the upper frame bodies and configured of an X-ray transmissive material such as cotton, carbon, or the like, is further detachably covered with the cover 5A, such as a fabric made of a thick texture, excellent in durability. The main body 5 and the cover 5A both have flexibility. To the lower frame bodies 18 at the four corners for supporting the seat portion 2, the backrest portion 3 and the armrests 11 are mounted by fixing screws 17 detachably and approximately perpendicular to the ground plane of the wheels. The rear wheels 8 have, as well as the front wheels 7, a diameter of 6 inches (15.3 cm) and arranged at lower ends of the lower frame bodies 18. The front and rear wheels are located on extended lines of the lower frame bodies. The lower-frame-body expansion and contraction fittings 14 are mounted not only to upper portions of the front wheels 7 but also to the upper portions of the rear wheels 8. The rear wheels 8 rotate in the back-and-forth direction only (do not rotate about an axis of a support pipe). The fixing screws 17 face inwardly of the wheelchair.

Herein, as long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the brakes may not be mounted to the rear wheels. The diameter of the rear wheels may not be 6 inches, and may be appropriately changed within the range of 6 to 12 inches (15.3 to 30.5 cm), for example. The rear wheels, as well as the front wheels, may rotate 360 degrees about the axis of the support pipe. The wheelchair may be a folding wheelchair such that the center of the seat portion is lifted to be folded.

Figure 3:
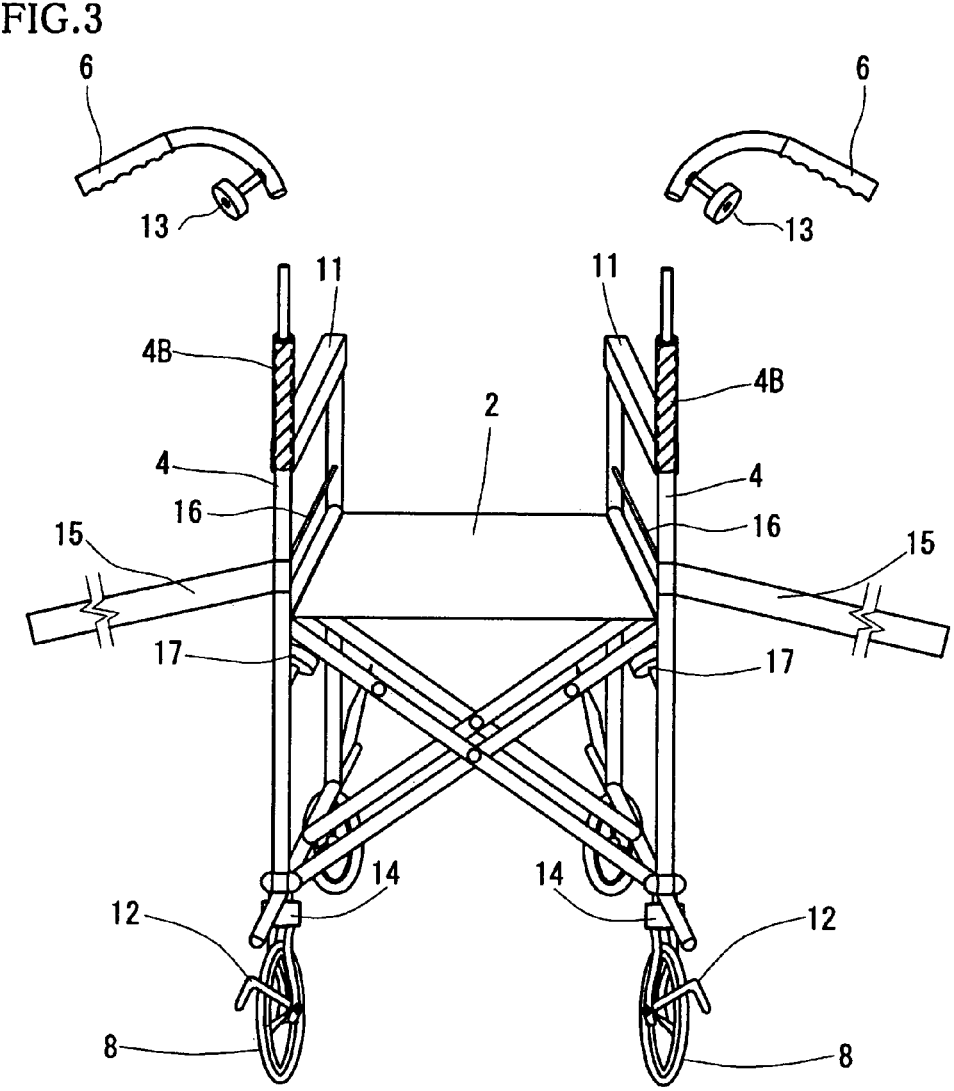
FIG. 3 is a schematic rear view showing one example of the wheelchair, in which a main body of a backrest portion is removed, to which the present invention is applied.

FIG. 3 is a schematic rear view showing one example of the wheelchair to which the present invention is applied, in which the main body of the backrest portion is removed. The holding portions are removed from the upper frame bodies of the backrest portion by loosening the holding-portion adjustment knobs. The two holding portions are each oriented to right and left directions or a forward direction relative to the wheelchair, for example, and mounted back to the upper frame bodies. To the upper frame bodies of the backrest portion, elastic upper frame body covers 4B are mounted. Herein, as long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the upper frame body covers may not necessarily be mounted to the upper frame bodies of the backrest portion.

Figure 4:
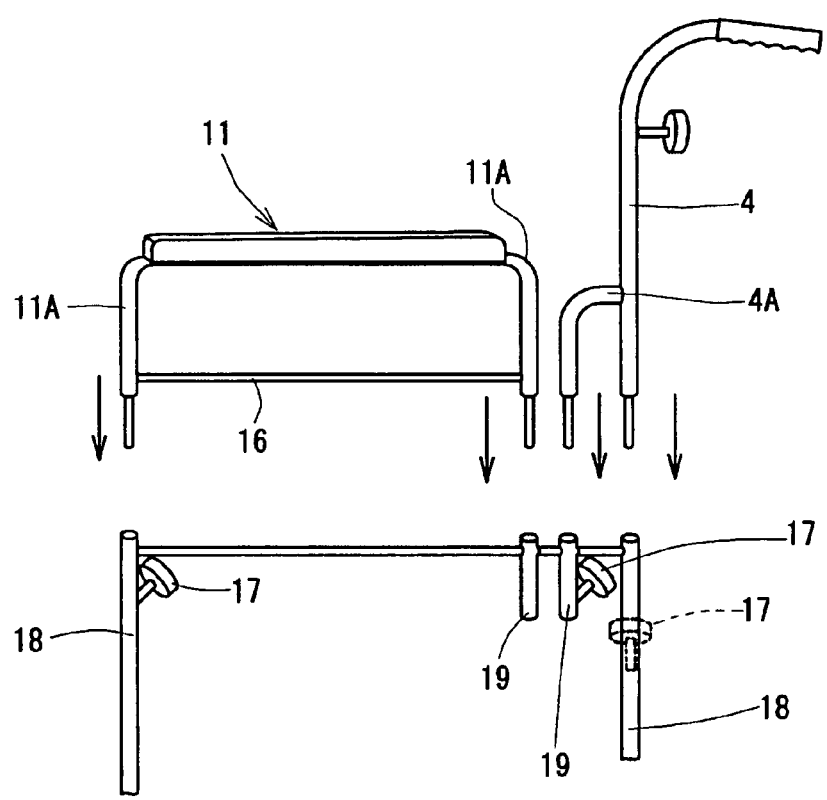
FIG. 4 is a schematic lateral view showing one example of another mode of an armrest and a backrest portion of the wheelchair to which the present invention is applied.

FIG. 4 is a schematic lateral view showing one example of another mode of the armrest and the backrest portion of the wheelchair to which the present invention is applied. In FIG. 4, the armrest 11 and the upper frame body 4 of the backrest portion are kept apart. An upper branched frame body 4A for reinforcement is branched from the upper frame body 4 and extends approximately parallel to the upper frame body 4. The upper frame body 4 and the upper branched frame body 4A are each detachably mounted by the fixing screws 17 to the lower frame body 18 and an accommodating pipe 19 arranged approximately parallel to the lower frame body 18. The two frame members 11A of the armrest 11 are each detachably mounted to the lower frame body 18 and the accommodation pipe 19 arranged approximately parallel to the lower frame body 18. Between the frame members 11A of the armrest 11, the reinforcement pipe 16 for connecting these members is arranged.

Herein, as long as the upper frame body of the backrest portion is approximately perpendicular to the ground plane of the wheel, the main body of the backrest portion is detachably mounted and configured of an X-ray transmissive material, and the holding portion is installed consecutively to the upper frame body detachably and turnably, the armrest and the upper frame body of the backrest portion may not necessarily be kept apart and the fixing screw may not necessarily be mounted to the accommodating pipe.

Figure 5:
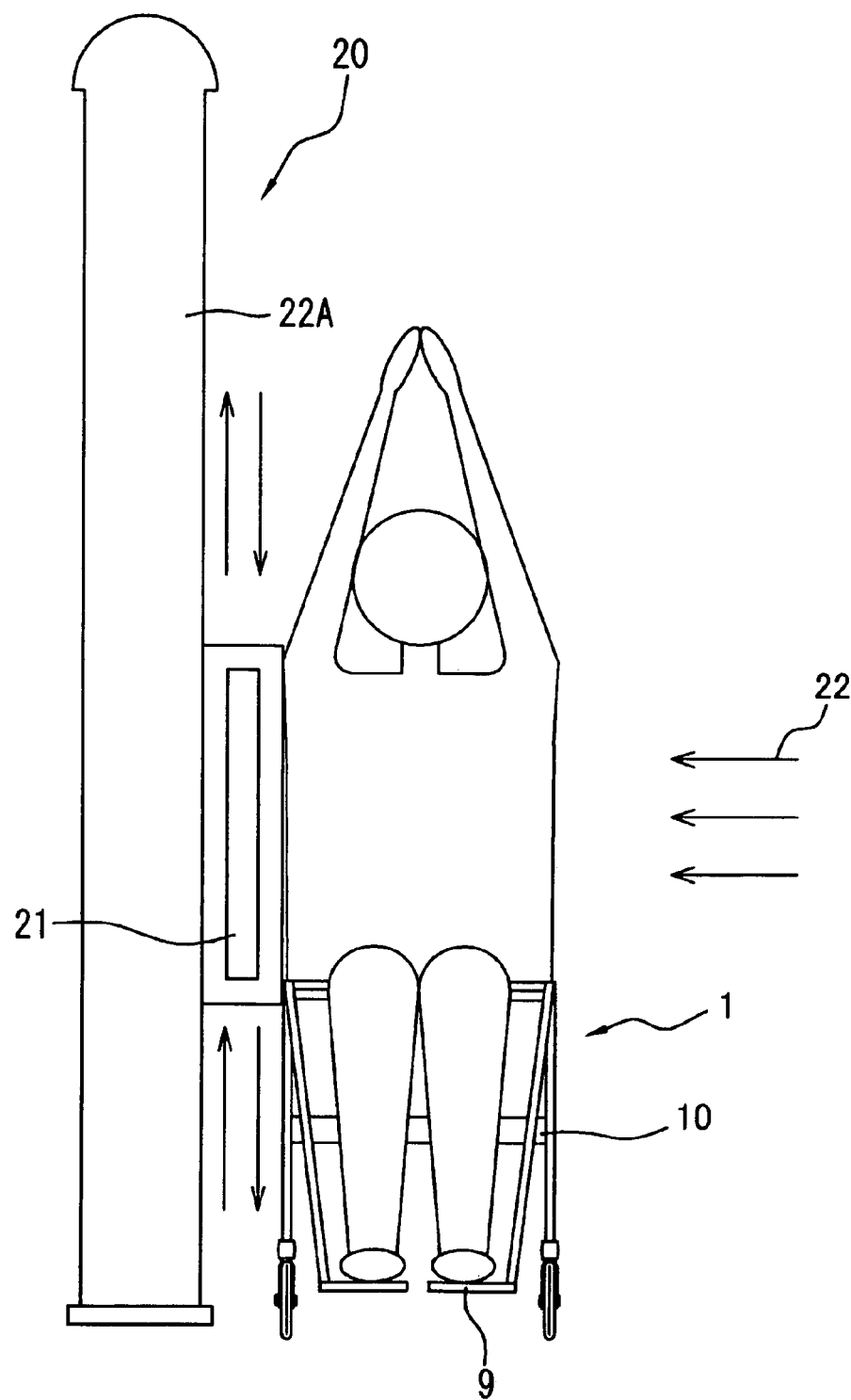
FIG. 5 is a schematic explanatory diagram showing one example of a state in which performed is radiography in the lateral direction while sitting in the wheelchair to which the present invention is applied.

FIG. 5 is a schematic explanatory diagram showing one example of a state in which radiography in the lateral direction is performed while being seated in the wheelchair to which the present invention is applied. When radiography in the lateral direction is performed, the fixing screws are loosened to remove the right and left armrests and the backrest portion, and a lateral side of a body of a radiographed person who sits in the wheelchair to which the present invention is applied and the cassette (image receiving portion) 21 of Lieder's radiographic stand 20 are brought approximately parallel and adhere to each other. An X-ray tube (not shown) arranged laterally of the radiographed person is orientated so that an X-ray radiation direction 22 is approximately perpendicular to the cassette (image receiving portion) 21. An X-ray radiated from the X-ray tube (not shown) passes through the body of the radiographed person, and the image is exposed to the cassette (image receiving portion) 21. As a result, a radiogram is obtained. The cassette (image receiving portion) moves vertically along a radiographic unit support device 22A corresponding to each radiographed region such as a chest region, a head region, a neck region, a shoulder, a lumbar region, or the like. As long as the radiogram is obtained, an imaging plate (IP) may be used instead of the film-contained cassette. Of course, it is possible that the fixing screws are loosened to remove the right and left armrests and the backrest portion, and in this state, the back of the radiographed person and the image receiving portion of Lieder's radiographic stand are brought approximately parallel and adhere to each other, and then, radiography in the anteroposterior direction is performed.

Figure 6:
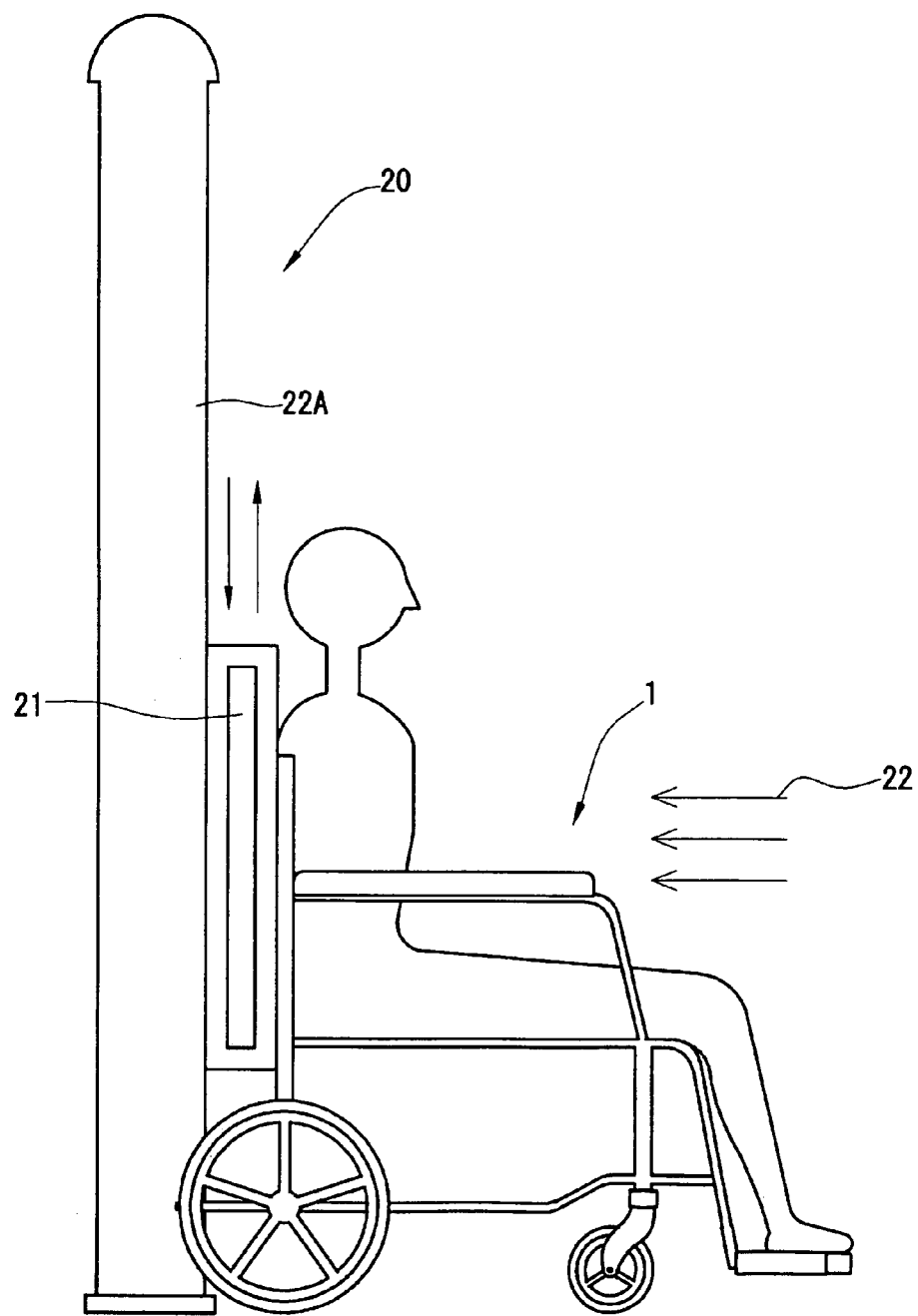
FIG. 6 is a schematic explanatory diagram showing a state in which performed is radiography in the anteroposterior direction while sitting in the wheelchair to which the present invention is applied.

FIG. 6 is a schematic explanatory diagram showing a state in which radiography in the anteroposterior direction is performed while being seated in the wheelchair to which the present invention is applied. In radiographing, the holding portions are removed from the wheelchair 1 to which the present invention is applied and the fabric made of a thick texture that covers the main body of the backrest portion is removed so that only the main body is left. The back of the radiographed person who sits in the wheelchair to which the present invention is applied and the cassette (image receiving portion) 21 of Lieder's radiographic stand 20 are brought approximately parallel and adhere to each other. An X-ray radiated from an X-ray tube (not shown) arranged forward of the radiographed person into the X-ray radiation direction 22 passes through the body of the radiographed person and the main body of the backrest portion, and the image is exposed to the cassette (image receiving portion) 21. As a result, a radiogram is obtained. The cassette (image receiving portion) moves vertically along the radiographic unit support device 22A corresponding to each radiographed region such as a chest region, a head region, a neck region, a shoulder, a lumbar region, or the like. At this time, the holding portions are removed. However, as long as the back of the radiographed person can adhere to the image receiving portion, the holding portions may not necessarily be removed. The holding portions may be turned so as to be positioned on the same plane as the backrest portion or be oriented forward of the backrest portion.

Further, the back of the radiographed person adheres to the cassette (image receiving portion) 21. Thus, even for a radiographed person in a bent-over position, that is, a person whose back is bent forward, the upper body is naturally upright, and thus, it becomes possible to easily and exactly correct his or her posture. In addition, the upright posture of the upper body provides an image with a wide field of view and without distortion. Since a stationary radiographic stand installed in the regular location is used to radiograph, an exact X-ray incident angle can be obtained. As a result, an image with reproducibility can be provided.

Figure 7:
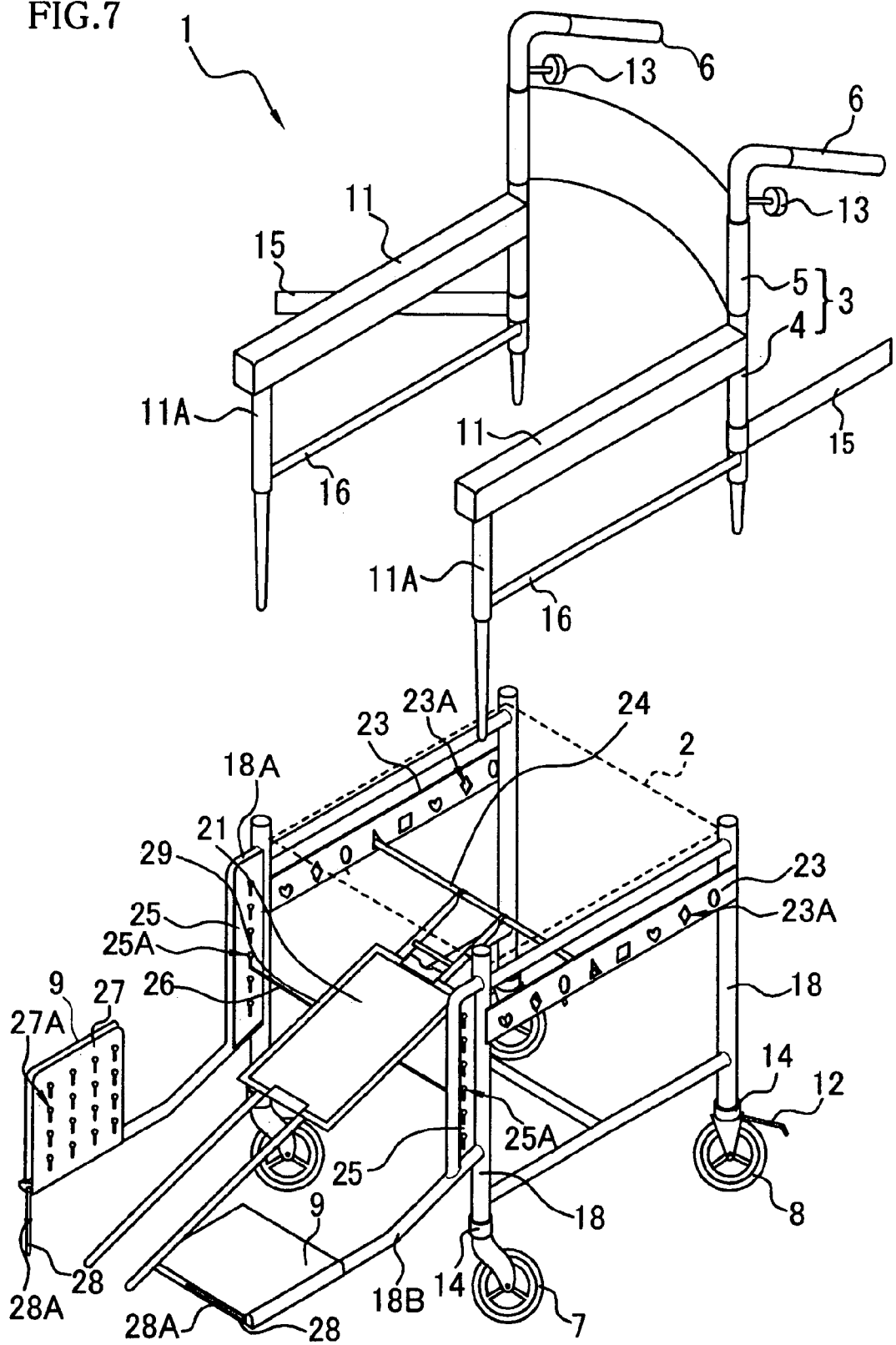
FIG. 7 is a schematic explanatory diagram showing one example of a state in which a cassette (image receiving portion) is mounted to a third example of the wheelchair to which the present invention is applied.

FIG. 7 is a schematic explanatory diagram showing one example of a state in which the cassette (image receiving portion) is mounted to a third example of a wheelchair to which the present invention is applied.

In FIG. 7, the wheelchair 1 to which the present invention is applied is configured of: the seat portion 2; the backrest portion 3 including the upper frame bodies 4 mounted approximately perpendicular to the seat portion and the main body 5 mounted to the upper frame bodies transversely of the upper frame bodies; holding portions 6 installed consecutively to the upper frame bodies in a manner to backwardly protrude from the same plane as the upper frame bodies; the front wheels 7; the rear wheels 8 to which the brakes 12 are mounted; the footrests 9 for supporting feet; the armrests 11 including the frame members 11A approximately parallel to the upper frame bodies; the holding-portion adjustment knobs 13 capable of turning the holding portions and removing the holding portions; the lower-frame-body expansion and contraction fittings 14 for expanding and contracting the lower frame bodies; the seatbelts 15 configured of an X-ray transmissive material such as cotton, carbon, or the like; the reinforcement pipes 16 for connecting the upper frame bodies 4 and the frame members 11A of the armrests 11; the lower frame bodies 18 approximately perpendicular to the ground plane of the wheels; leg frame bodies 18B for interconnecting the front-side lower frame bodies and the footrests; first support members 23 arranged below the seat portion so that each support member is opposed to each other, in which a first rod member 24 (one example of a first lateral member), arranged in an opposed spatial area, is detachably mounted to one of a plurality of first holes 23A; second support members 25 arranged forward of the front-side lower frame bodies so that each support member is opposed to each other, in which a second rod member 26 (one example of a second lateral member), arranged in an opposite spatial area, is detachably mounted to one of a plurality of keyhole-shaped second holes 25A; supporting plates 27, each of which is mounted on a surface opposed to a surface of the footrest 9 on which the foot is placed, having thereon a plurality of keyhole-shaped holes 27A so that holding members for holding the cassette (image receiving portion) can be mounted; and footrest support rods 28, mounted to the footrests and including height adjustment devices 28A, for supporting the footrests. The cassette (image receiving portion) 21 is held by a cassette holder 29, hooks of the end of the cassette holder are hinged on the first rod member 24, and the cassette holder 29 is placed on the second rod member 26.

The cassette holder used herein means one that includes a cassette holding-down portion and a cassette receiving portion in which the cassette holding-down portion and the cassette receiving portion can be moved up and down according to the size of the cassette (image receiving portion), and screws mounted to cylindrical rods on the both sides are loosened and the cassette (image receiving portion) is moved up and down to adjust the position of the cassette (image receiving portion) for fixture.

One portion of the frame members 11A inserted into the front-side lower frame bodies 18 is longer than that of the upper frame bodies 4 inserted into the rear-side lower frame bodies 18. The first holes 23A next to one another differ in shape, and the first holes 23A opposed to each other are the same in shape. Further, when the main body of the backrest portion and the seat portion are transparent, it becomes possible to confirm the position of the radiographic unit through the main body, thereby, making it easy to adjust positioning of the backrest portion to the radiographic unit. It is also possible to confirm through the seat portion the position of the cassette (image receiving portion) arranged immediately below the seat portion, and thus, it becomes easy to position the cassette (image receiving portion).

The wheelchair to which the present invention is applied may be configured not only of a metal material but also of wood, an acrylic material, an X-ray transmissive material such as carbon, for example.

The upper frame bodies of the backrest portion are approximately perpendicular to the ground plane of the wheels. Further, a fabric or the main body 5 of the backrest portion, which is detachably mounted to the upper frame bodies and configured of an X-ray transmissive material such as cotton, carbon, or the like, is detachably covered with a cover (not shown) excellent in durability, such as a fabric made of a thick texture. The main body and the cover both have flexibility. To the lower frame bodies 18 at the four corners for supporting the seat portion 2, the backrest portion 3 and the armrests 11 are mounted detachably and approximately perpendicular to the ground plane of the wheels. The rear wheels 8 have, as well as the front wheels 7, a diameter of 6 inches (15.3 cm) and are arranged at lower ends of the lower frame bodies 18. The front and rear wheels are located on extended lines of the lower frame bodies. Not only to the upper portions of the front wheels 7 but also to the upper portions of the rear wheels 8, the lower-frame-body expansion and contraction fittings 14 are mounted. The rear wheels 8 rotate in the back-and-forth direction only (do not rotate about the axes of the lower frame bodies).

Herein, as long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the fabric configured of the X-ray transmissive material may not necessarily be covered detachably with the fabric excellent in durability. Alternatively, the main body may not necessarily be a fabric. Further, the holding portion adjustment instruments, the lower-frame-body expansion and contraction fittings, the seatbelts, the support plates, and the footrest support rods may not be mounted to the wheelchair. The rear wheels may not be provided with the brakes, and the diameter of the rear wheels may not be 6 inches and may be appropriately changed within the range of 6 to 12 inches (15.3 to 30.5 cm), for example. The rear wheels, as well as the front wheels, may rotate 360 degrees about the axes of the lower frame bodies. The holding portions may not necessarily protrude backward, and may be located on the extended lines of the upper frame bodies, or protrude forward of the upper frame bodies, for example. Further, the wheels may not necessarily be located on the extended lines of the lower frame bodies, and may be arranged on the inside so that the wheels are located below the seat portion, for example.

As long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the wheelchair may be a folding wheelchair such that the center of the seat portion is lifted to be folded. The lower-frame-body expansion and contraction fittings expand and contract the lower frame bodies by threads on the surfaces of the lower frame bodies and inner screws of the lower-frame-body expansion and contraction fittings. However, the lower frame bodies may be expanded and contracted by making members different in height exchangeable.

As long as the first lateral member and the second lateral member are detachably mounted to the first support members and the second support members, respectively, the first holes and the second holes may not necessarily be formed. The first lateral member and the second lateral member may be mounted by magnetism, for example, and alternatively, upper sides of the first support members may be formed with a plurality of grooves. As long as the first lateral member is arranged in the opposed spatial region, the first lateral member may not necessarily be continued from the first support member on one side to the opposed first support member on the other side.

Upon movement in the wheelchair, for the reason that it becomes possible to seat a person sitting in the wheelchair more stably, it is preferable that in addition to the seatbelts configured of an X-ray transmissive material such as cotton, carbon, or the like, a seatbelt configured of a fabric made of a thick texture be mounted to the wheelchair.

As long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the leg-rest may be mounted so that the leg frame bodies 18B on the right and left are connected.

Figure 8:
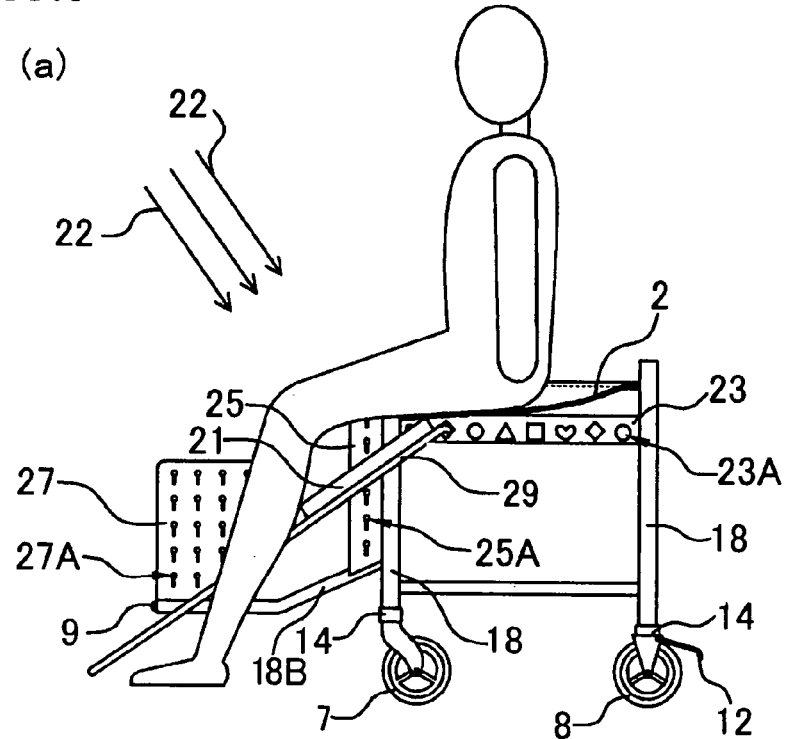
FIG. 8 are schematic diagrams of (a) one embodiment for radiographing near a flexed knee that cannot be straightened in the anteroposterior direction by using the third example of the wheelchair to which the present invention is applied; and (b) another embodiment for radiographing a thigh in the anteroposterior direction by using the third example of the wheelchair to which the present invention is applied.
Figure 8:
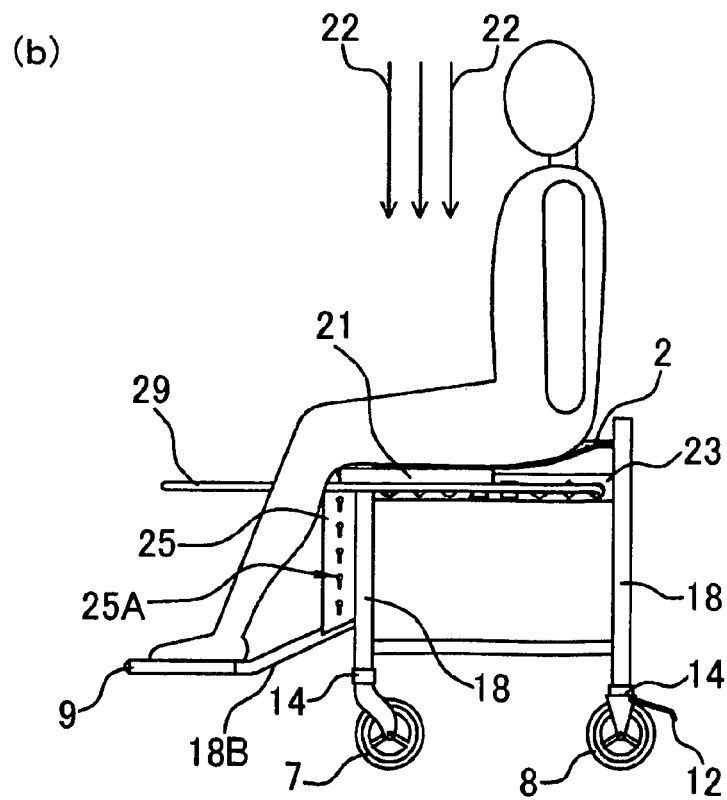

FIG. 8(a) is a schematic view of one embodiment in which a portion near a flexed knee that cannot be straightened is radiographed in the anteroposterior direction, by using the third example of the wheelchair to which the present invention is applied.

FIG. 8(b) is a schematic view of one embodiment in which a thigh is radiographed in the anteroposterior direction, by using the third example of the wheelchair to which the present invention is applied. In FIG. 8(a) and FIG. 8(b), the lower frame bodies or the like on the near side are omitted.

As shown in FIG. 8(a), when the portion near the knee is radiographed in the anteroposterior direction, in the first holes 23A formed below the seat portion 2 and in the first support members 23 arranged between the front-and-rear lower frame bodies 18, the first rod member (not shown) is mounted, in the second holes 25A formed in the second support members 25 arranged between the front-side lower frame bodies 18 and the lower branched frame bodies 18A branched forward of the front-side lower frame bodies, the second rod member (not shown) is mounted, and the cassette holder 29 for holding the cassette (image receiving portion) 21 has the hooks at its ends hinged on the first rod member (not shown), and is placed on the first rod member (not shown) and the second rod member (not shown). A radiographing person positions the first rod member (not shown) so that the cassette (image receiving portion) 21 is placed at a portion near the back of the knee of the radiographed person, and adjusts the front and rear positions of the cassette (image receiving portion) 21 by a screw, or changes the position of the second rod member (not shown) to adjust the height of the cassette (image receiving portion) 21.

As shown in FIG. 8(b), when the thigh is radiographed in the anteroposterior direction, the seat portion 2 is configured of an X-ray transmissive material such as cotton, carbon, or the like, the first rod members (not shown) are mounted to at least two of a plurality of first holes 23A, and on these first rod members (not shown), the cassette holder 29 on which held is the cassette (image receiving portion) 21 is placed. Thereby, the cassette (image receiving portion) 21 is arranged immediately below and approximately parallel to the seat portion 2, and the radiographing person adjusts the position and the orientation of the X-ray tube (not shown) so that the X-ray radiation direction 22 is approximately perpendicular to the cassette (image receiving portion) 21 while the radiographed person remains seated on the seat portion 2. In FIG. 8(a) and FIG. 8(b), the armrests or the upper frame bodies are removed. However, it is a matter of course that radiography can be performed while these components remain mounted.

Herein, the X-ray radiated from the X-ray tube (not shown) arranged above the radiographed person passes through the body of the radiographed person, and the X-ray image is exposed on the cassette (image receiving portion) 24. As a result, a radiographic image is obtained. As long as the radiographic image is obtained, the cassette (image receiving portion) may be a cassette containing a radiographic film. Alternatively, an imaging plate (IP), or an image reading device that does not require the cassette (image receiving portion) may be used.

As long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the seat portion may not necessarily be configured of the X-ray transmissive material.

Figure 9:
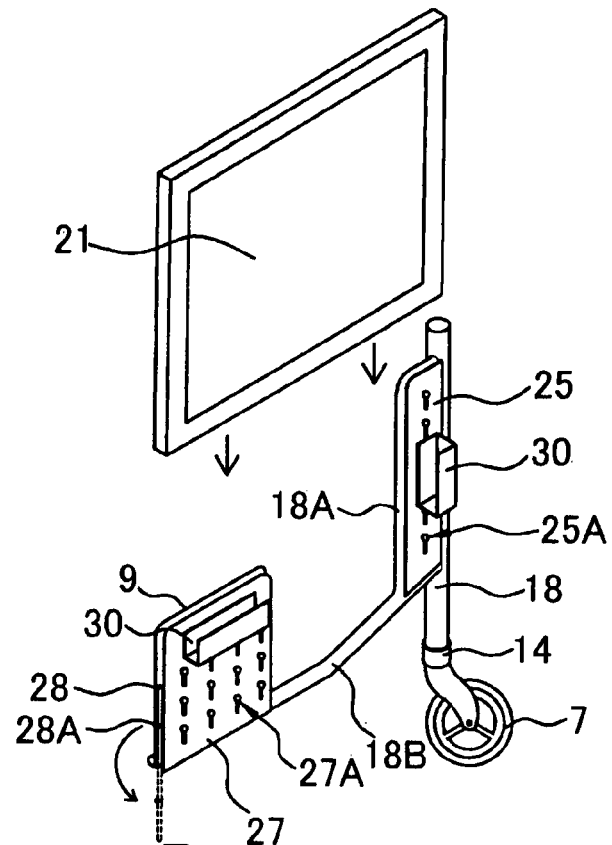
FIG. 9 are schematic diagrams of (a) one example for mounting the cassette (image receiving portion) for radiographing a lower limb in the lateral direction; and (b) another embodiment for radiographing the lower limb in the lateral direction by using the third example of the wheelchair to which the present invention is applied.
Figure 9:
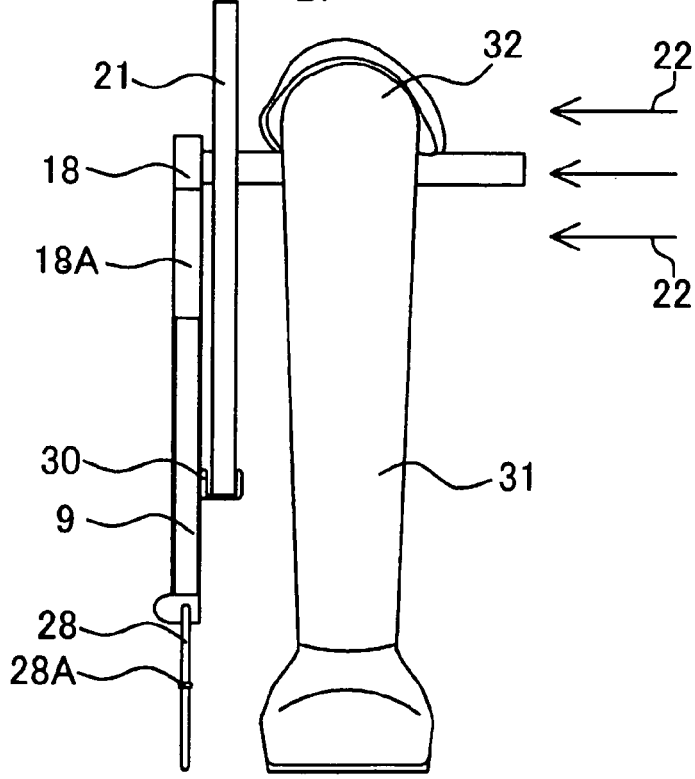

FIG. 9(a) is a schematic view showing one example in which mounted is the cassette (image receiving portion) for radiographing a lower limb in the lateral direction. FIG. 9(b) is a schematic view of one embodiment in which the lower limb in the lateral direction is radiographed by using the third example of the wheelchair to which the present invention is applied.

When radiographing the lower limb in the lateral direction, the footrest is turned so as to be approximately perpendicular to the ground plane, and the surface opposed to the surface on which the foot is placed is positioned on approximately the same plane as the second support member, the U-shaped holding members 30 for holding the cassette (image receiving portion) 21 are mounted to each of the second support member 25 and the support plate 27 mounted to the footrest 9 so that both of bottom surfaces of the holding members 30 are placed on approximately the same plane, that is, placed at approximately the same height, and the cassette (image receiving portion) is fitted into the two mounted holding members 30 to hold the cassette (image receiving portion). The holding members 30 are mounted by inserting hooks (not shown) mounted in the holding members into the keyhole-shaped holes 25A formed on the second support member 25 and the keyhole-shaped holes 27A formed on the support plate 27. Alternatively, the holding members 30 are mounted to holes selected from a plurality of keyhole-shaped holes formed on each of the second support member 25 and the support plate 27 according to a radiographed region of the lower limb and the size of the cassette (image receiving portion).

The footrest support rod 28 mounted along the lateral side of the footrest 9 is moved by 180 degrees to support the footrest, and thereby, the cassette (image receiving portion) can be held more stably. The footrest support rod 28 is provided with the height adjustment device 28A, in which the threads are utilized to rotate the height adjustment device 28A for a height adjustment. Thus, even when the holding member mounted to the support plate 27 of the footrest 9 and the holding member mounted to the second support member 25 differ in height, which results in tilting of the cassette (image receiving portion) 24, the height can be adjusted by the height adjustment device 28A to correct the tilt.

Herein, as long as the holding members can be mounted to the second support member 25 or the support plate 27, the keyhole-shaped holes may not necessarily be formed in the second support member or the support plate so that the hooks (not shown) of the holding members are inserted into these holes to mount the holding members. For example, the holding members may be mounted by magnetism.

When the cassette (image receiving portion) is held correspondingly to the radiographed region of the lower limb, the radiographing person brings the lower limb (a below-knee region 31 and a knee region 32) of the radiographed person close to the cassette (image receiving portion) 21, and allows the lower limb (the below-knee region 31 and the knee region 32) to adhere to the cassette (image receiving portion) so that the lower limb enters within the range of the cassette (image receiving portion). Subsequently, as shown in FIG. 9(b), the location and the orientation of the X-ray tube (not shown) are adjusted so that the X-ray radiation direction 22 is approximately perpendicular to the cassette (image receiving portion) to radiograph the lower limb. The lower limb shown herein includes the knee region and the below-knee region. When a tip of the foot or the like is radiographed, the foot is placed on the footrest so that the foot enters the range of the cassette (image receiving portion), and the position of the footrest is adjusted for radiography. A method for radiographing by adjusting the position of the footrest is also applied at the time of radiographing the lower limb in the anteroposterior (front) direction.

Subsequently, a description is given of Lieder's radiographic stand and Bucky's radiographic table.

Lieder's radiographic stand is installed approximately perpendicular to the floor surface, and mainly used for radiographing in a standing position or a sitting position. On the other hand, Bucky's radiographic table is installed approximately parallel to the floor surface, and mainly used for radiographing in a recumbent position. Both of the stand and the table are installed such that the X-ray from the X-ray tube is radiated in an exact direction relative to the image receiving surface of the radiographic unit and table. Some Bucky's radiographic tables can tilt the image receiving surface of the radiographic unit relative to the horizontal surface. Therefore, when the radiographic unit of such radiographic table or stand, or the like, is used to radiograph, an undistorted image picture with reproducibility can be obtained. Further, the use of an X-ray-amount automatic-exposure-control device built into Lieder's radiographic stand or Bucky's radiographic table permits radiographing with the appropriate amount of X-ray which is neither too much nor too little.

Figure 10:
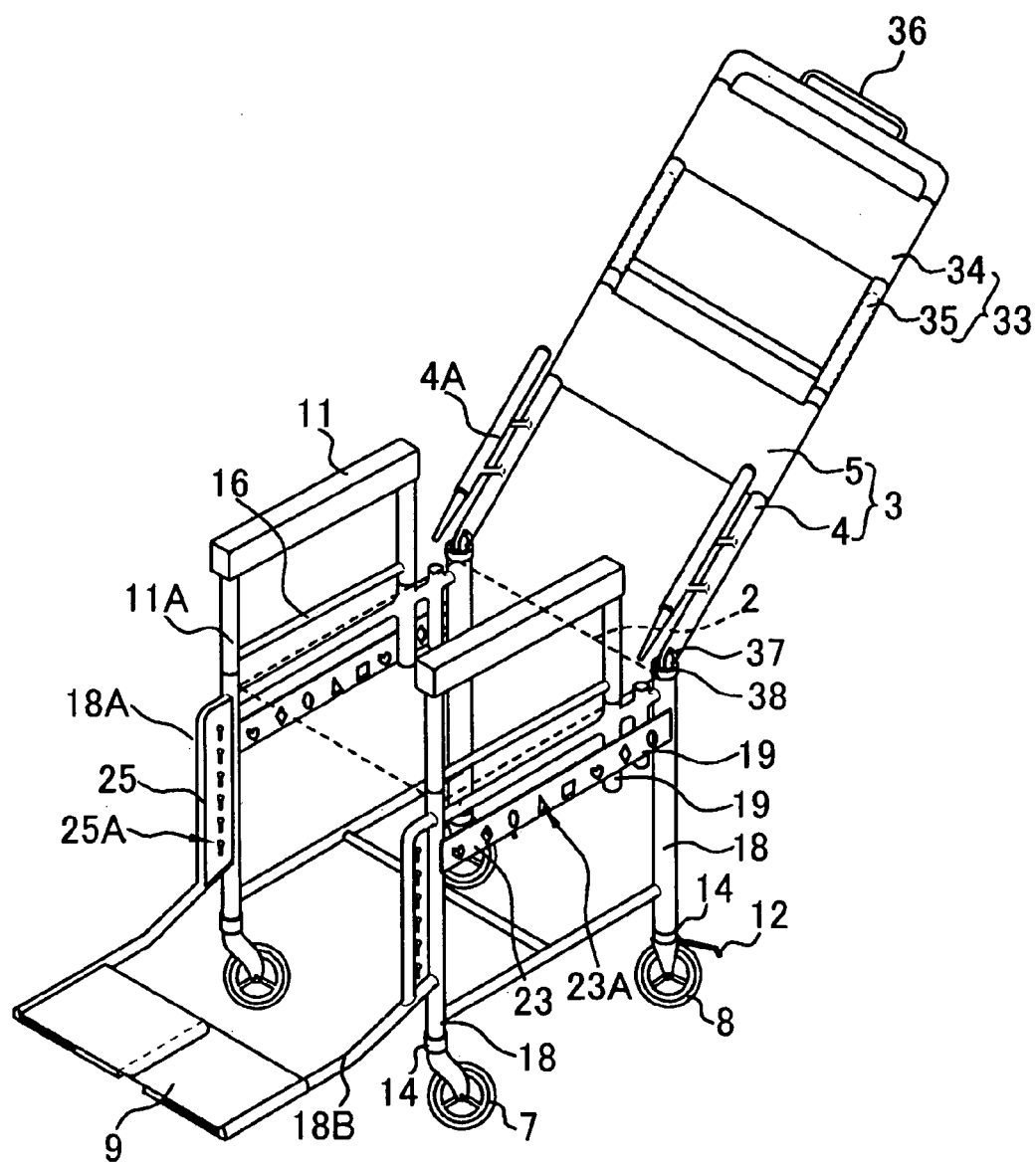
FIG. 10 is a schematic diagram showing a fourth example of a wheelchair to which the present invention is applied.

FIG. 10 is a schematic diagram showing a fourth example of the wheelchair to which the present invention is applied. The wheelchair to which the present invention is applied shown in FIG. 10 differs from that shown in FIG. 7 in that: the armrests 11 and the upper frame bodies 4 of the backrest portion 3 are kept apart and the upper frame bodies 4, at its ends, are arranged turnable relative to the seat portion 2 by joint portions 37; setscrews 38 for determining a tilting angle of the backrest portion 3 are mounted to the lower frame bodies 18; the upper branched frame bodies 4A for reinforcement are detachably mounted to the upper frame bodies 4 and extend approximately parallel to the upper frame bodies 4, and the upper frame bodies 4 and upper branched frame bodies 4A are each detachably mounted to the lower frame bodies 18 and the accommodating pipes 19 arranged approximately parallel to the lower frame bodies 18; there is a pillow portion 33 including a U-shaped pillow-portion frame body 35 detachably mounted to the upper frame bodies, and a headrest 34 detachably mounted to the pillow-portion frame body transversely of the pillow-portion frame body and configured of an X-ray transmissive material such as cotton, carbon, or the like; and there is a grip 36 mounted to the pillow portion frame body. When the pillow portion 33 is mounted, the holding portions are removed.

Figure 11:
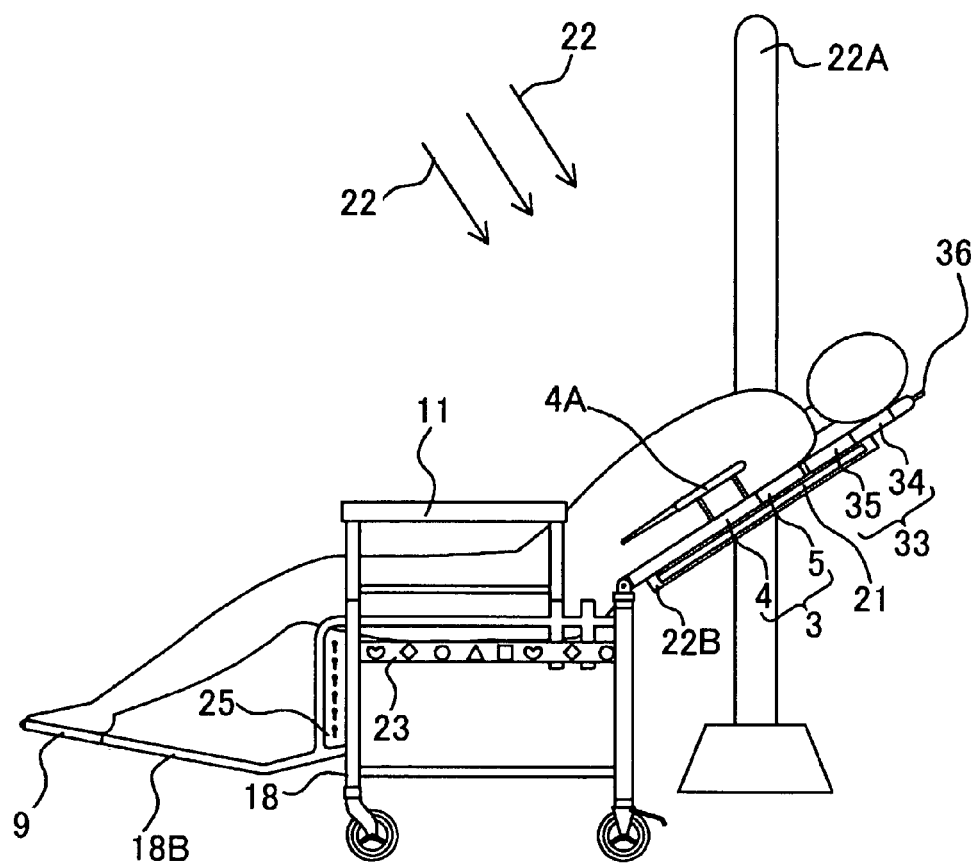
FIG. 11 is a schematic diagram showing one mode in which radiography is performed by tilting backward a backrest portion of the wheelchair to which the present invention is applied.

FIG. 11 is a schematic diagram showing one mode in which radiography is performed by tilting backward the backrest portion of the wheelchair to which the present invention is applied. In FIG. 11, the backrest portion 3 is placed on and approximately parallel to a radiographic unit 22B previously tilted, and the cassette (image receiving portion) is arranged inside of and approximately parallel to the radiographic unit 22B mounted to the radiographic unit support device 22A. When positioning, the radiographed person is not moved but the wheelchair in which the radiographed person sits and the image receiving portion are moved, and thus, the radiographed person may keep his or her back placed onto the backrest portion 3. The radiographing person adjusts the position and orientation of the X-ray tube (not shown) so that the X-ray radiation direction 22 is approximately perpendicular to the cassette (image receiving portion) 21. Alternatively, an X-ray tube arranged in such a manner to move in conjunction with the tilt of the radiographic unit so that the X-ray radiation direction 22 is approximately perpendicular to the cassette (image receiving portion) 21 may be used. In FIG. 11, the armrests are mounted. However, as a matter of course, it may be possible to radiograph by removing the armrests.

Figure 12:
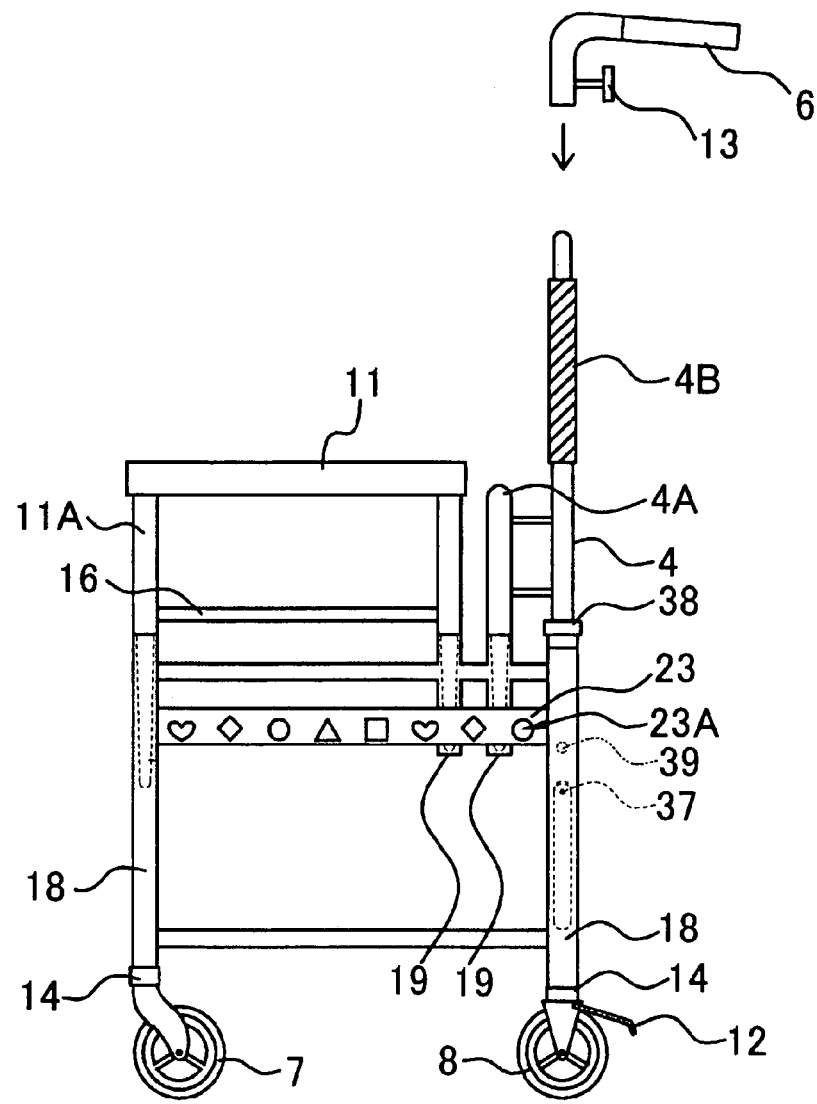
FIG. 12 is a schematic diagram showing one mode in which an armrest and a backrest portion kept apart are mounted to a lower frame body.

FIG. 12 is a schematic diagram showing one mode in which the armrests and the backrest portion kept apart are mounted to the lower frame bodies. The holding-portion adjustment knobs 13 are loosened to remove the holding portions 6 from the upper frame bodies 4 of the backrest portion. The two holding portions are each oriented in the right and left directions or forward direction of the wheelchair, for example, and mounted back to the upper frame bodies. To the upper frame bodies 4 of the backrest portion, the elastic upper frame body cover 4B is mounted. One portion of the upper frame bodies 4 is inserted into the inside of the lower frame bodies 18 and fixed by the fixing screw 39. One portion of the upper branched frame bodies 4A and one portion of the frame members 11A of the armrests 11 are each inserted into the accommodating pipes 19. As compared to one portion of the frame members 11A inserted into the accommodating pipes 19, one portion of the frame members 11A inserted into the lower frame bodies 18 is longer. Between the frame members 11A of the armrests 11, the reinforcement pipes 16 for connecting these members are arranged. Further, between the upper frame bodies 4 and the upper branched frame bodies 4A, a relatively hard plate such as an acrylic plate, wood, or the like, is fitted, and thus, it becomes possible to firmly support the back of the radiographed person at the time of radiographing the chest region and other lateral directions.

Herein, as long as the holding portions are installed consecutively to the upper frame bodies detachably and turnably, the holding portions may not be removed from the upper frame bodies of the backrest portion. For example, the holding portions may be turned so that the holding portions remain unremoved. As long as the upper frame bodies of the backrest portion are approximately perpendicular to the ground plane of the wheels, the main body of the backrest portion is detachably mounted and configured of an X-ray transmissive material, and the holding portions are installed consecutively to the upper frame bodies detachably and turnably, the upper frame body cover may not necessarily be mounted to the upper frame bodies of the backrest portion.

Figure 13:
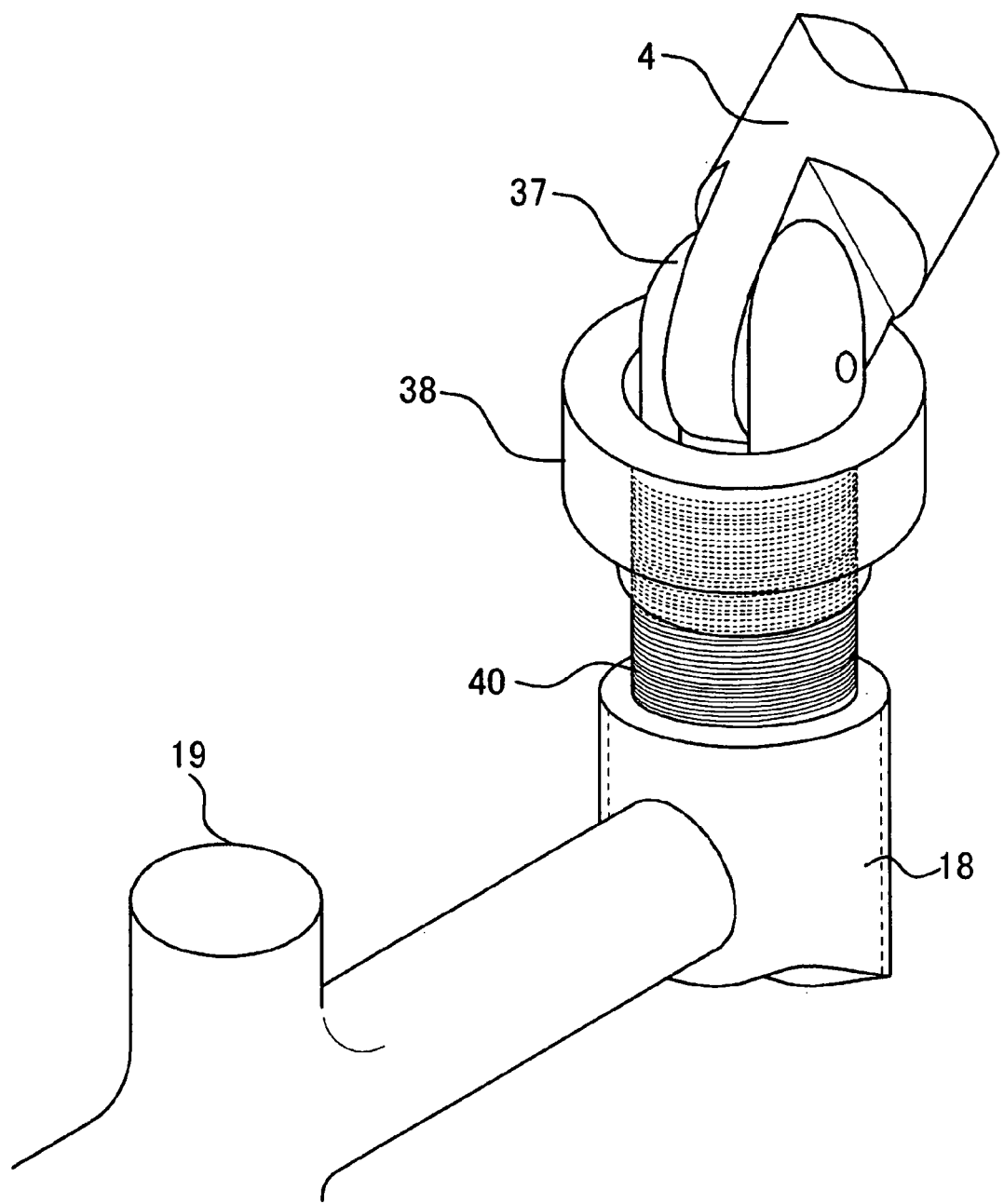
FIG. 13 is an enlarged schematic view of a joint portion and a setscrew.

FIG. 13 is an enlarged schematic view of the joint portion and the setscrew. When the backrest portion 3 is backwardly tilted as shown in FIG. 10, one portion of the upper frame bodies 4 inserted into the inside of the lower frame bodies 18 as shown in FIG. 12 and the joint portions 37 are lifted upward and extracted from the inside of the lower frame bodies 18, and backwardly tilted about the joint portions 37. Thereby, the upper frame bodies 4 abut against the setscrews 38 so that the angle is determined. One portion on the surfaces of the lower frame bodies 18 is formed with the threads 40, and the threads are engaged with threads (not shown) on the inside of the setscrews 38. In this state, the setscrews 38 are rotated to move up and down thereby to adjust the angle. That is, when the setscrews 38 are moved downward, the angle of the upper frame bodies 4 relative to axes of the lower frame bodies 18 is large, and in reverse, when the setscrews 38 are moved upward, the angle of the upper frame bodies 4 relative to the axes of the lower frame bodies 18 is small. Alternatively, when setscrews different depending on predetermined angles are mounted beforehand at the lower frame bodies so that the upper frame bodies 4 are tilted at predetermined angles such as 30 degrees, 45 degrees, and 60 degrees, for example, the setscrews 38 may not be moved up and down to adjust the angle.

Figure 14:
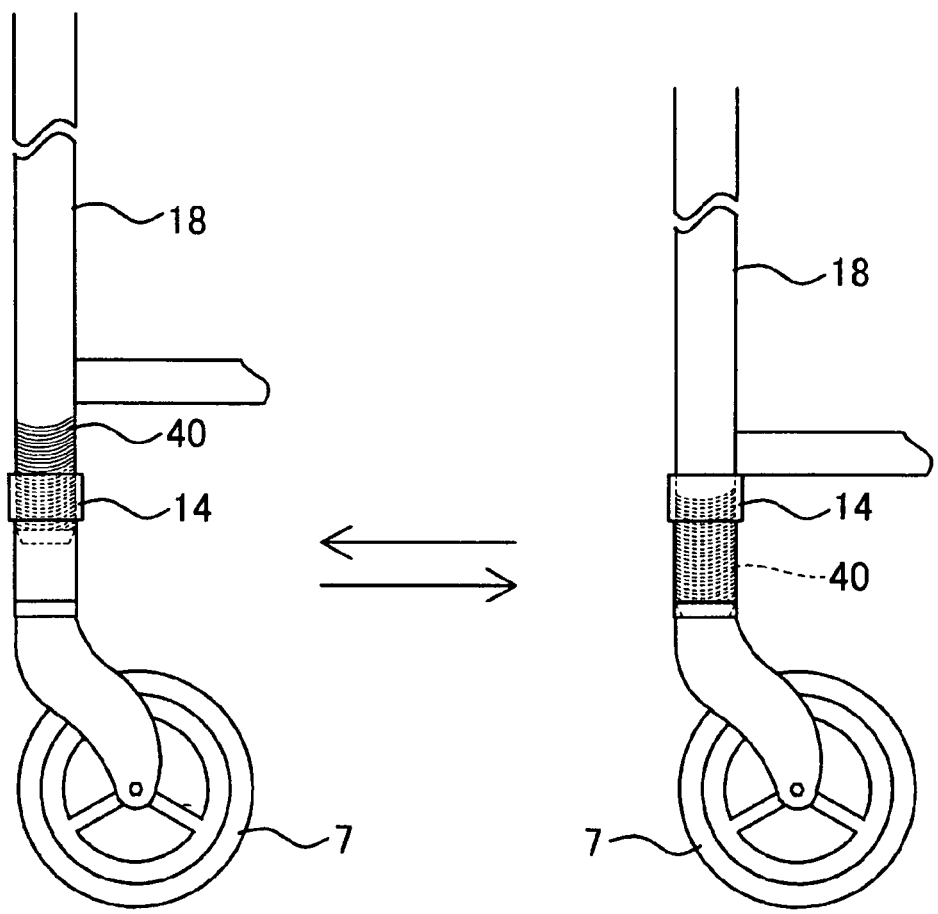
FIG. 14 is a schematic view showing one example of a state in which a lower frame body mounted to a front wheel is expanded and contracted.

FIG. 14 is a schematic view showing one example of a state in which the lower frame body mounted to the front wheel is expanded and contracted. One portion of the surfaces of the lower frame bodies 18 is formed with the threads 40, and the threads are engaged with threads (not shown) on the inside of the lower-frame-body expansion and contraction fittings 14. In this state, the front wheels 7, together with the lower-frame-body expansion and contraction fittings 14, are rotated to expand and contract the lower frame bodies 18. The same is true of a case where the lower frame bodies mounted to the rear wheels are expanded and contracted. Herein, as long as the lower frame bodies can be expanded and contracted, its operation may be manually or electrically performed. Further, the threads may not necessarily be formed. For example, locking screws formed at ends of the lower frame bodies are hooked on inner walls of the lower-frame-body expansion and contraction fittings, and in this state, the lower-frame-body expansion and contraction fittings are turned by approximately ¼ in the right and left directions to switch on or off of the locking thereby to expand and contract the lower frame bodies.

Figure 15:
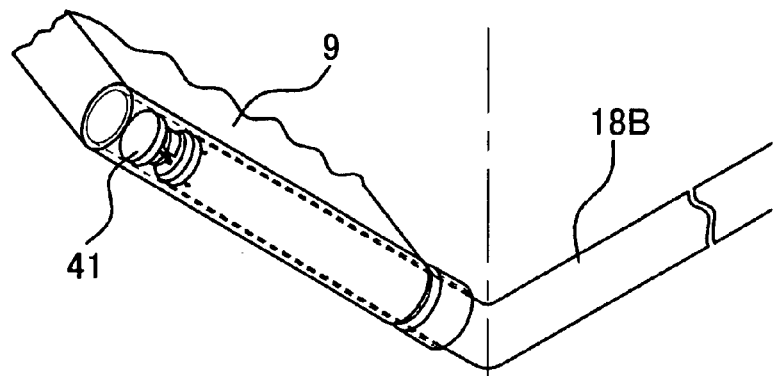
FIG. 15 are schematic views showing (a) one example of a footrest and (b) a state in which the footrest is moved forward.
Figure 15:
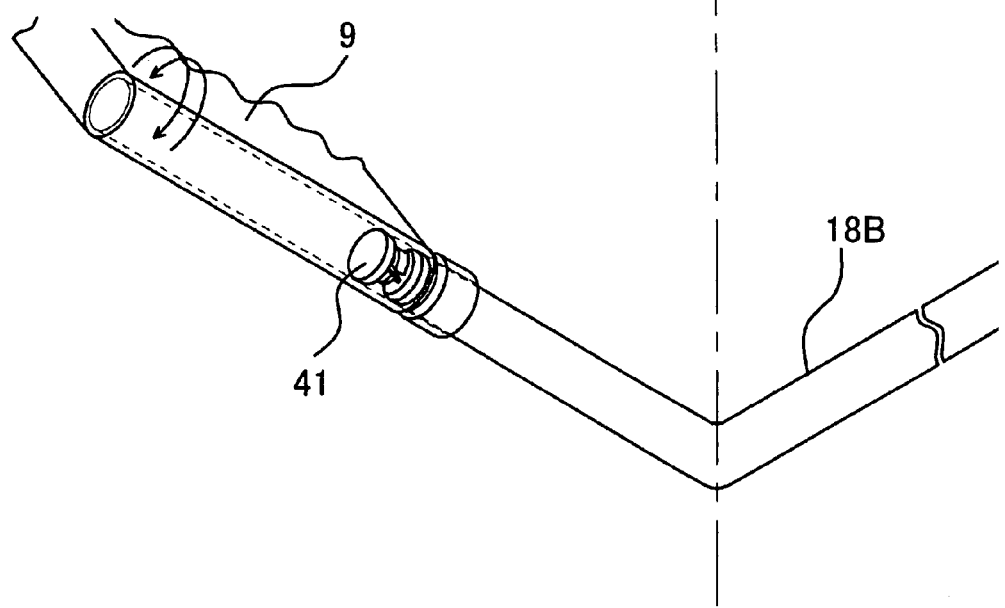

FIG. 15(a) is a schematic view showing one example of the footrest. FIG. 15(b) is a schematic view showing a state in which the footrest is moved forward. The distal end of the leg frame body 18B is formed with a locking screw 41, and one side of the footrest 9 is a cylindrical body. One portion of the leg frame body 18B including the locking screw 41 is inserted into the cylindrical body. The cylindrical body is configured such that the locking screw 41 is hooked on the inner wall of the cylindrical body of the footrest 9 so that the footrest 9 is not removed from the leg frame body 18B completely. One portion of the cylindrical body of the footrest is turned by approximately ¼ in the right and left directions to permit switch on or off of the locking. Thereby, the footrest 9 slides along the leg frame body 18B, and thus, the footrest can be moved forward.

Figure 16:
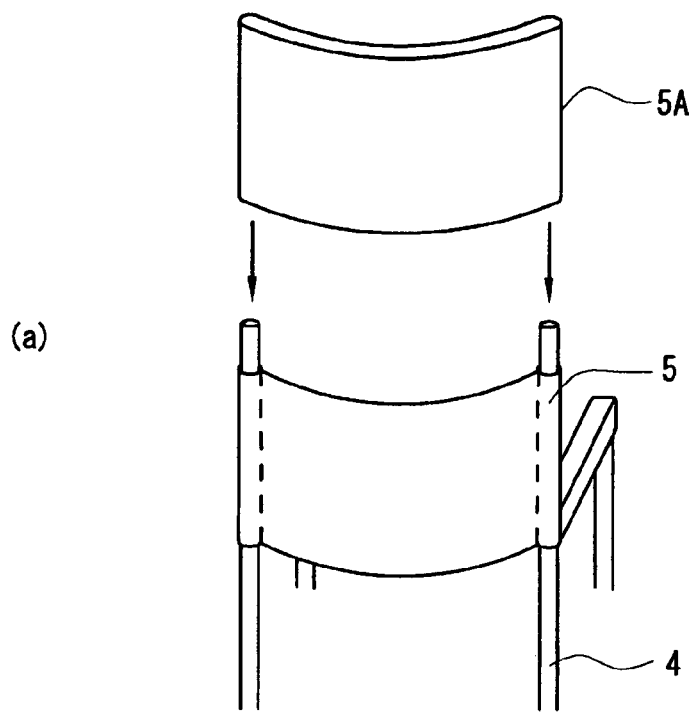
FIG. 16 are schematic diagrams showing (a) one mode in which the main body of the backrest portion is covered with a cover configured of a material excellent in durability; and (b) one mode in which the main body of the backrest portion has been covered with the cover configured of the material excellent in durability.
Figure 16:
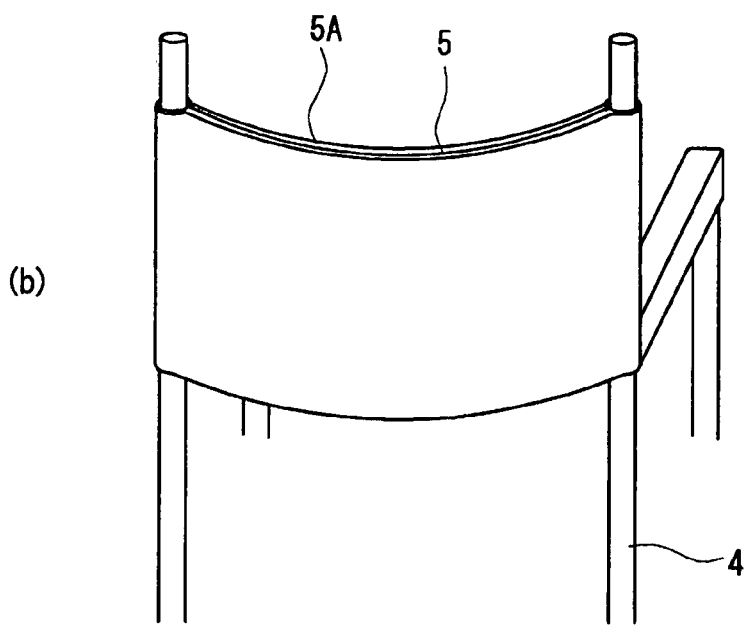
Figure 17:
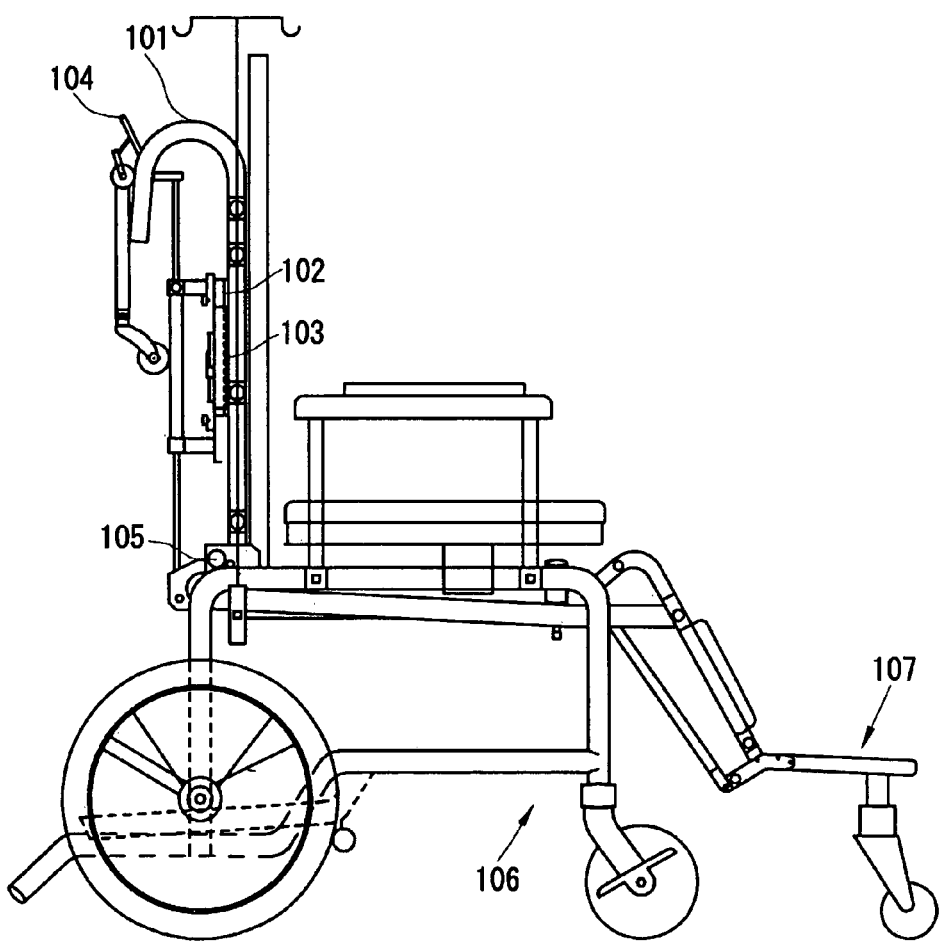
FIG. 17 is an entire schematic view of a conventional radiography-use wheelchair.

FIG. 16(a) is a schematic view showing one mode in which the main body of the backrest portion is covered with a cover configured of a material excellent in durability. FIG. 16(b) is a schematic view showing one mode in which the main body of the backrest portion has been covered with the cover configured of the material excellent in durability. Both the main body 5 of the backrest portion and the cover 5A have flexibility. Herein, as long as the main body of the backrest portion is detachably covered with the cover, the cover may take any form, and a band-shaped cover may be possible, for example.

As described above, in the wheelchair to which the present invention is applied, the upper frame bodies of the backrest portion are approximately perpendicular to the ground plane of the wheels, the main body of the backrest portion is detachably mounted to the upper frame bodies of the backrest portion and is configured of an X-ray transmissive material, and the holding portions are installed consecutively to the upper frame bodies detachably and turnably. Because of this configuration, the radiographed person who sits in the wheelchair to which the present invention is applied can bring Lieder's radiographic stand and the body of the radiographed person approximately parallel and adhere to each other. As a result, it becomes possible to radiograph a chest region, a head region, a neck region, a shoulder, a lumbar region, a pelvic region, an upper limb, a lower limb, and other regions, without a need to switch to a different chair such as a radiography-dedicated wheelchair, a chair arranged before Lieder's radiographic stand, or other relevant wheelchairs.

In the conventional radiography-use wheelchairs, the radiographing person needs to position the radiographed person who sits in the wheelchair in a cramped space within the wheelchair by moving the radiographed person so that the radiographed person is approximately parallel to the radiographic unit. In particular, it is difficult for the radiographed person to orient his or her body in the oblique or lateral direction so that radiographing in the oblique direction or the lateral direction is performed. However, in the wheelchair to which the present invention is applied, the wheelchair in which the radiographed person sits is moved to position the wheelchair. Thus, a burden of the radiographed person is lessened. The upper frame bodies of the backrest portion are approximately perpendicular to the ground plane of the wheels, the main body of the backrest portion is detachably mounted to the upper frame bodies of the backrest portion and is configured of an X-ray transmissive material, and the holding portions are installed consecutively to the upper frame bodies detachably and turnably. In this way, the wheelchair is configured such that radiography can be performed by allowing the radiographed person, and Lieder's radiographic stand or Bucky's radiographic table or the like to adhere. Moreover, the wheelchair is lightweight and small in size, easy to use, and comfortable, as compared to the conventional radiography-use wheelchair. Further, the lower frame bodies are approximately perpendicular to the ground plane of the wheels, the backrest portion and the right and left armrests are installed consecutively to the lower frame bodies detachably and approximately perpendicular to the ground plane of the wheels, and the wheels are mounted on the extended lines of the lower frame bodies. Thus, the side surface of the wheelchair can adhere to Lieder's radiographic stand, and as a result, it becomes possible to easily and exactly make a radiographic positioning simply by orienting or moving the wheelchair itself obliquely or laterally while the backrest portion and the armrests do not stand in the way. It is possible to radiograph the radiographed person not only in the anteroposterior direction but also in the lateral direction or the oblique direction while he or she remains seated in the wheelchair. Thus, the present wheelchair is particularly suitable for radiography using Lieder's radiographic stand or Bucky's radiographic table or the like.

Further, as a result of radiographing by using Lieder's radiographic stand, Bucky's radiographic table, or the like, it becomes possible to obtain a more exact radiographing condition. It is also possible to perform radiography or fluoroscopy on a fluoroscopic stand or table or Lieder's radiographic stand to which a cassette support apparatus is mounted, which enables radiography or diagnosis in a wider range. It is also possible to use Bucky's radiographic table installed stationary horizontal to the floor surface or a radiographic table or stand in which the angle of the radiographic unit can be changed.

The wheelchair of the present invention is provided with first support members each arranged below the seat portion so as to face each other and having a first lateral member arranged in the opposed spatial area being detachably mounted, and second support members each arranged forward of the front-side lower frame bodies so as to face each other and having a second lateral member arranged in the opposed spatial area being detachably mounted. Thus, it is possible to support the cassette (image receiving portion) used for radiography near the back of the knee of the radiographed person who sits in the wheelchair. It is also possible to radiograph the lower limb without a need to switch to a different chair such as a radiography-dedicated wheelchair, a chair arranged before Lieder's radiographic stand, or the like. In particular, the second lateral member detachably mounted to the second support members can adjust the height of the cassette (image receiving portion). Essentially, the knee needs to be straightened and adhere to the cassette (image receiving portion) for radiographing, and when radiographing a flexed knee that cannot be straightened, an auxiliary device needs to be employed in order to bring the back of the knee close to the cassette (image receiving portion) as much as possible. However, in the wheelchair of the present invention, it is possible to bring the back of the knee close to the cassette (image receiving portion) without using the auxiliary device and to perform excellent radiography of the knee in the anteroposterior (front) direction.

In the wheelchair to which the present invention is applied, the adjacent first holes formed in the first support members differ in shape to each other. Thus, it is easy to understand the back-and-forth position of the first rod member. Further, the opposed first holes are the same in shape to each other. Thus, after the first rod member is inserted into the first hole on one side, it is easy to find the opposed first hole on the other side.

Each of the back-and-forth and right-and-left lower frame bodies is configured to be expandable and contractable. Thus, even when a wheel of the wheelchair rides up over Lieder's radiographic stand or the like and the seat portion is tilted relative to the ground plane, in this case, the lower frame bodies to which the rode-up wheel is mounted are shortened or the lower frame bodies to which the non-ridden-up wheels are mounted are expanded, and so forth, to bring the seat portion approximately parallel to the ground plane. When getting off from the wheelchair, for example, the front-side lower frame bodies are contracted or the rear-side lower frame bodies are expanded, and thus, the wheelchair is tilted so that the front end of the seat portion is at a lower level of the rear end of the seat portion, which permits easily getting off from the wheelchair. Alternatively, when seated in the wheelchair, the front-side lower frame bodies are expanded or the rear-side lower frame bodies are contracted, and thus, the wheelchair is tilted so that the front end of the seat portion is at a higher level of the rear end of the seat portion, which makes it difficult for a buttocks to shift forward. It is further possible to adjust the height from the ground plane to the seat portion according to a manner to tilt the front and rear sides of the seat portion in the upward or downward direction. This adjustment provides a sharp radiogram in a wide range.

The armrests and the upper frame bodies of the backrest portion are kept apart, and the upper frame bodies are, at its ends, arranged to be turnable relative to the seat portion by the joint portions and are detachably arranged relative to the seat portion. This arrangement permits tilting of the backrest portion in the backward direction, and thus, it becomes possible for a person who sits in the wheelchair to assume a relaxed posture while traveling. Alternatively, it is possible to radiograph a person who finds difficulty in maintaining a sitting position by using the existing radiographic table or stand while the person remains seated in the wheelchair in a semi-sitting or a recumbent position at the time of not only traveling but also radiographing. When the upper frame bodies are abutted against the setscrews mounted to the lower frame bodies, and the setscrews are moved up and down, the tilting angle of the upper frame bodies can be adjusted.

The footrests are turned to be approximately perpendicular to the ground plane and the surfaces opposed to the surfaces on which the feet are placed are positioned on approximately the same plane as the second support members, and the support plates on which a plurality of keyhole-shaped holes are formed are mounted to the surfaces opposed to the surfaces of the footrests on which the feet are placed. Thus, it is possible to mount the holding members for holding the cassette (image receiving portion) in the holes. Similarly, the holding members mounted to the holes of the second support members on which the keyhole-shaped holes are formed can be used to arrange the cassette (image receiving portion) on the lateral side of the lower limb along the side surface of the wheelchair. As a result, it is possible to radiograph the lower limb in the lateral direction.

The footrests are movably mounted to the leg frame bodies. Thus, even when a tall radiographed person sits, the footrests can be moved to place his or her feet on the footrests even while the legs are stretched. As a result, the knee position is lowered, which makes it easier to radiograph the lower limb. It also becomes possible to adjust the length by matching the position of the feet at the time of being reclined.

The seat portion is configured of the X-ray transmissive material, and thus, it is possible to radiograph the thigh by arranging the cassette (image receiving portion) immediately below the seat portion by the first support members.

Further, between the upper frame bodies and the upper branched frame bodies, a relatively hard plate such as an acrylic plate, wood, or the like, can be fitted from above, and thus, it becomes possible to firmly support the back of the radiographed person.

The backrest portion and the right and left armrests can be removed. Thus, it becomes easy for a wheelchair user to move from a bed to the wheelchair and from the wheelchair to the bed or Bucky's radiographic table or the like.

The main body of the backrest portion and the cover that covers the main body are a flexible fabric that is detachable. Thus, when the fabric becomes dirty, the fabric can be replaced by a new one, and the fabric can be brought into a shape that matches the rounded back of the person who sits in the wheelchair. Therefore, a comfortable posture can be maintained. Alternatively, the fabric is flexible, which permits easy attachment and detachment.

To the upper frame bodies of the backrest portion, the elastic upper frame body cover is mounted. Thus, when the wheelchair to which the present invention is applied is allowed to adhere to Lieder's radiographic stand, a shock caused to the radiographed person can be alleviated and Lieder's radiographic stand can be protected from the shock caused due to contact with the upper frame bodies.

The seatbelts configured of the X-ray transmissive material are mounted. Thus, it becomes easy for the radiographed person to maintain a posture suitable for radiographing at the time of radiography. Further, another seatbelt configured of a fabric made of a thick texture can also be mounted. Thus, it becomes possible to seat the person who sits in the wheelchair more stably upon traveling in the wheelchair.

The front wheels and the rear wheels are arranged at the lower ends of the lower frame bodies approximately perpendicular to the ground plane of the respective wheels. Thus, there is no protrusion in the lateral side of the wheelchair, and as a result, it becomes possible to adhere the wheelchair to the image receiving portion. At the time of radiographing by using Lieder's radiographic stand, the image receiving portion can freely slide up and down along the lateral side of the radiographed person and that of the wheelchair, which permits obtaining of a sharp radiogram in a wide range. Alternatively, Lieder's radiographic stand or Bucky's radiographic table can be used, and thus, it is possible to radiograph under excellent radiographic conditions.

The front wheels and the rear wheels can rotate by 360 degrees about the axes of the lower frame bodies, and thus, it becomes possible to make a detailed movement of the wheelchair upon positioning for radiography.

The invention claimed is:

1. A wheelchair, comprising:
   a seat portion; a
   a backrest portion provided with backrest columns mounted approximately perpendicular to the seat portion and a main body detachably mounted to the backrest columns transversely of the backrest columns, said main body being made of an X-ray transmissive material;
   holding portions detachably installed consecutively to the backrest columns, said holding portions being turnable so as to permit positioning of said holding portions generally on a same plane as the backrest portion while remaining installed to the backrest columns;
   wheels, the backrest columns being arranged approximately perpendicular to a ground plane of the wheels;
   front lower columns connected to respective ones of the wheels, approximately perpendicular to the ground plane of the wheels; and
   rear lower columns connected to remaining respective ones of the wheels, approximately perpendicular to the ground plane of the wheels, the backrest columns being installed consecutively and linearly to the rear lower columns.

2. The wheelchair according to claim 1, wherein the seat portion is approximately parallel to the ground plane of the wheels.

3. The wheelchair according to claim 1, further comprising right and left armrests including armrest columns mounted approximately perpendicular to the seat portion, wherein:
   the backrest columns are detachably installed approximately perpendicular to the ground plane of the wheels to the rear lower columns,
   the armrest columns are detachably and consecutively installed approximately perpendicular to the ground plane of the wheels to the front lower columns, and
   the wheels are respectively mounted on extended lines of the front lower columns and the rear lower columns.

4. The wheelchair according to claim 1, wherein backrest branched columns are mounted to the backrest columns, and a space is formed between the backrest columns and the backrest branched columns.

5. The wheelchair according to claim 1, wherein:
   the holding portions are curved, and
   holding-portion adjustment knobs operable to selectively allow turning of the holding portions and allow removal of the holding portions are mounted to the holding portions in a direction approximately the same as a direction into which the holding portions are curved.

6. The wheelchair according to claim 1, wherein:
   the main body is detachably covered with a cover, and
   the main body and the cover have flexibility.

7. The wheelchair according to claim 1, further comprising:
   right and left armrests including armrest columns mounted approximately perpendicular to the seat portion;
   leg members extended forward from the front lower columns;
   footrests mounted to the leg members;
   first support members each arranged below the seat portion so as to face each other and having a first lateral member arranged in an opposed spatial area being detachably mounted; and second-support members each arranged forward of the front lower columns so as to face each other and having a second lateral member arranged in an opposed spatial area being detachably mounted.

8. The wheelchair according to claim 7, wherein:

the main body is detachably covered with a cover, the backrest columns are detachably installed approximately perpendicular to the ground plane of the wheels to the rear lower columns, the armrest columns are detachably and consecutively installed approximately perpendicular to the ground plane of the wheels to the front lower columns, and the wheels are respectively mounted on extended lines of the front lower columns and the rear lower columns.

9. The wheelchair according to claim 7, wherein each of the front lower columns and the rear lower columns is configured to be expandable and contractable.

10. The wheelchair according to claim 7, wherein:

the right and left armrests and the backrest columns are separate from one another, and the backrest columns are, at ends thereof, arranged to be detachable and turnable relative to the seat portion.

11. The wheelchair according to claim 7, wherein:

the footrests are turnably mounted to the leg members, the footrests have surfaces on which feet are placed and surfaces opposed to the surfaces on which the feet are placed, the surfaces opposed to the surfaces on which the feet are placed are configured to have holding members for holding a cassette (image receiving portion) being detachably mounted thereon, and when the footrests are turned so as to be approximately perpendicular to the ground plane, the surfaces opposed to the surfaces on which the feet are placed are located on approximately the same plane as the second support members.

12. The wheelchair according to claim 7, wherein the footrests are movably mounted to the leg members.

13. The wheelchair according to claim 7, wherein the seat portion is made of an X-ray transmissive material.

14. The wheelchair according to claim 7, wherein:

the first support members are formed with a plurality of holes, the holes next to one another differ in shape, and the holes opposed to each other are the same in shape.

15. The wheelchair according to claim 1, wherein no structural portion of the wheelchair which is disposed above the wheels protrudes beyond a back surface of said main body, such that said back surface of main body is contactable with a cassette (image receiving portion) vertically arranged behind a patient seated in the seat portion.

16. The wheelchair according to claim 1, wherein said main body is removable from said backrest columns while said backrest columns remain attached to said rear lower columns.

* * * * *